(12) United States Patent
Huang et al.

(10) Patent No.: US 7,939,115 B2
(45) Date of Patent: May 10, 2011

(54) DIETARY SUPPLEMENT AND RELATED METHOD

(75) Inventors: Ruo G. Huang, Long Beach, CA (US); Stephen R. Missler, Grand Rapids, MI (US); Marc J. P. Lemay, Long Beach, CA (US); Edward W. Kahler, Anaheim, CA (US); Donald J. Pusateri, Hemet, CA (US); Haeri Roh-Schmidt, Long Beach, CA (US); Shyam Ramakrishnan, Long Beach, CA (US)

(73) Assignee: Access Business Group International LLC, Ada, MI (US)

( * ) Notice: Subject to any disclaimer, the term of this patent is extended or adjusted under 35 U.S.C. 154(b) by 247 days.

(21) Appl. No.: 12/059,868

(22) Filed: Mar. 31, 2008

(65) Prior Publication Data

US 2008/0226744 A1 Sep. 18, 2008

Related U.S. Application Data

(63) Continuation-in-part of application No. 10/915,784, filed on Aug. 11, 2004, now Pat. No. 7,416,749, which is a continuation-in-part of application No. 10/360,789, filed on May 7, 2002, now Pat. No. 6,989,161, and a continuation-in-part of application No. 09/878,377, filed on Jun. 12, 2001, now Pat. No. 6,511,675.

(60) Provisional application No. 60/210,746, filed on Jun. 12, 2000.

(51) Int. Cl.
*A61K 36/752* (2006.01)
*A61K 36/53* (2006.01)
*A61K 36/00* (2006.01)

(52) U.S. Cl. .......................... 424/736; 424/745; 424/725

(58) Field of Classification Search ........................ None
See application file for complete search history.

(56) References Cited

U.S. PATENT DOCUMENTS

| | | |
|---|---|---|
| 5,356,636 A | 10/1994 | Schneider et al. |
| 5,401,502 A | 3/1995 | Wunderlich et al. |
| 5,514,382 A | 5/1996 | Sultenfuss |
| 5,578,336 A | 11/1996 | Monte |
| 5,612,039 A | 3/1997 | Policappelli et al. |
| 5,654,011 A | 8/1997 | Jackson et al. |
| 5,686,108 A | 11/1997 | Pusateri et al. |
| 5,770,217 A | 6/1998 | Kutilek, III et al. |
| 5,807,586 A | 9/1998 | Jackson et al. |
| 5,830,887 A | 11/1998 | Kelly |
| 5,840,278 A | 11/1998 | Coleman |
| 5,882,646 A | 3/1999 | Pusateri et al. |
| 5,904,924 A | 5/1999 | Gaynor et al. |
| 5,948,443 A | 9/1999 | Riley et al. |
| 5,955,102 A | 9/1999 | Gorenbein et al. |
| 5,972,985 A | 10/1999 | Thomas et al. |
| 5,976,548 A | 11/1999 | Hsia et al. |
| 5,976,568 A | 11/1999 | Riley |
| 5,985,338 A | 11/1999 | Suh et al. |
| 6,022,901 A | 2/2000 | Goodman |
| 6,087,391 A * | 7/2000 | Weidner .......................... 514/458 |
| 6,203,818 B1 | 3/2001 | Vester |
| 6,231,866 B1 | 5/2001 | Mann |
| 6,238,672 B1 * | 5/2001 | Chen .............................. 424/728 |
| 6,261,598 B1 | 7/2001 | Runge et al. |
| 6,352,712 B1 * | 3/2002 | Lukaczer et al. ............... 424/439 |
| 6,375,993 B1 * | 4/2002 | Aviram et al. .................. 424/744 |
| 6,440,410 B1 | 8/2002 | Yegorova |
| 6,440,467 B2 | 8/2002 | Mann |
| 6,551,628 B1 | 4/2003 | Watson et al. |
| 6,579,544 B1 * | 6/2003 | Rosenberg et al. ............ 424/736 |
| 6,586,018 B1 | 7/2003 | Fasano |
| 6,638,545 B1 | 10/2003 | Rombi |
| 6,676,978 B1 | 1/2004 | Nair |
| 2001/0012525 A1 | 8/2001 | Mann |
| 2002/0044980 A1 | 4/2002 | Castelli et al. |
| 2002/0119173 A1 | 8/2002 | Lin et al. |
| 2002/0168429 A1 | 11/2002 | Mann |
| 2002/0192314 A1 | 12/2002 | Cho et al. |
| 2003/0049335 A1 | 3/2003 | Stier et al. |
| 2003/0108627 A1 | 6/2003 | Selzer et al. |
| 2003/0162297 A1 | 8/2003 | Ou et al. |
| 2003/0228384 A1 | 12/2003 | Kurk et al. |

(Continued)

FOREIGN PATENT DOCUMENTS

EP 0906761 10/1998

(Continued)

OTHER PUBLICATIONS

DW ACC 1997-00655, Nov. 1996, DE 19612047 and, Kuehn.*
DW ACC 1991-171175, May 1991, Derwent, Evans et al.*
Ebringer A, et al, Rheumatoid arthritis: proposal for the use of antimicrobial therapy in early cases, Scand J Rheumatol, 32(1):2-11 (2003) (abstract only).
Rossi, A, et al, Protective effects of anthocyanins from blackberry in a rat model of acute lung inflammation, Free Radic Res, 37(8):891-900 (Aug. 2003) (abstract only).
Roy, S, et al, Anti-angiogenic property of edible berries, Free Radic Res, 36(9):1023-31 (Sep. 2002) (abstract only).

(Continued)

*Primary Examiner* — Christopher R Tate
*Assistant Examiner* — Randall Winston
(74) *Attorney, Agent, or Firm* — Warner Norcross & Judd LLP

(57) ABSTRACT

A composition including a unique combination of fruits, vegetables, herbs, and optionally vitamins, minerals and specialty ingredients. The composition can include a fruit ingredient, a vegetable ingredient and an herbal ingredient, wherein the fruit ingredient is at least one of pomegranate and citrus bioflavonoids, wherein the vegetable ingredient, is at least one of asparagus, lutein, lycopene and watercress, and wherein the herbal ingredient is at least one of basil, oregano and rosemary. The composition can be administered to subjects to correct a dietary deficiency of phytochemicals and other nutrients, improve plasma concentrations of antioxidant nutrients, and increase the activity of genetic mechanisms for DNA repair and stability.

9 Claims, 10 Drawing Sheets

U.S. PATENT DOCUMENTS

| | | | |
|---|---|---|---|
| 2004/0076692 A1 | 4/2004 | Van Norren et al. |
| 2005/0244518 A1 | 11/2005 | Huang et al. |
| 2006/0147563 A1 | 7/2006 | Huang et al. |
| 2008/0226744 A1 | 9/2008 | Huang et al. |

FOREIGN PATENT DOCUMENTS

| | | |
|---|---|---|
| JP | 2001-086954 | 4/2001 |
| JP | 2001-095529 | 4/2001 |
| WO | WO 0064282 | 4/2000 |
| WO | WO 0045829 | 8/2000 |
| WO | 0074697 | 12/2000 |
| WO | 2005/087208 | 9/2005 |

OTHER PUBLICATIONS

Youdim, KA, et al, Potential role of dietary flavonoids in reducing microvascular endothelium vulnerability to oxidative and inflammatory insults, J Nutr Biochem, 13(5):282-288 (May 2002) (abstract only).

Callicci, L, et al, Effects of gamma-irradiation on the free radical and antioxidant contents in nine aromatic herbs and spices, J Agric Food Chem, 51(4):927-34 (2003) (abstract only).

Dragland, Steinar, et al, Several culinary and medicinal herbs are important sources of dietary antioxidants, J Nutr, 133(5) 1286-90 (May 2003) (abstract only).

Kris-Etherton, Penny M, et al, Bioactive compounds in foods: their role in the prevention of cardiovaScular disease and cancer, Am J Med, 113 Suppl 9B 71S-88S (Dec. 30, 2002) (abstract only).

Tan, DX, et al, Significance of melatonin in antioxidative defense system: reactions and products, Biological Signals and Receptors, 9 (3-4) 137-59 (May-Aug. 2000) (abstract only).

Kahkonen, MP, et al, Antioxidant activity of plant extracts containing phenolic compounds, J Agr Food Chem, 47(10) 3954-62 (Oct. 1999) (abstract only).

Dragsted, LO, et al, Dietary levels of plant phenols and other non-nutritive components: could they prevent cancer?, European J Cancer Prev, 6(6) 522-8 (Dec. 1997) (abstract only).

Fejes, S, et al, Investigation of the in vitro antioxidant effect of *Petroselinum crispum*, Acta Pharm Hung, 68(3): 150-6 (1998) (abstract only).

Logia: Back to the Garden, downloaded from http://www.logia.net/products/back_to_garden.html (Jul. 20, 2004).

Foerster, SB et al, California's "5 a day—for better health!" campaign: an innovative population-based effort to effect large-scale dietary change, Am J Prev Med Mar.-Apr. 1995; 11 (2): 124-31.

Kant, AK, et al, A propsective study of diet quality and mortality in woman; JAMA Apr. 26, 2000; 283 (16): 2109-15.

Hennekens, CH, et al, Antioxidant vitamin-cardiovascular disease hypothesis is still promising, but still unproven; the need for randomized trials; Am J Clin Nutr Dec. 1995; 62 (6 Suppl): 1377S-1380S.

Parnetti, L , et al, Role of homocysteine in age-related vascular and non-vascular diseases, Aging (Milano) Aug. 1997; 9 (4): 241-57.

Brigelius-Flohe, R, et al; Vitamin E: function and metabolism; FASEB J Jul. 1999; 13 (10): 1145-55.

International Search Report, International Application No. PCT/US2009/036147, International Filing Date Mar. 5, 2009.

Written Opinion of the International Searching Authority, International Application No. PCT/US2009/036147, International Filing Date Mar. 5, 2009.

Duthie, Susan J et al, Antioxidant supplementation decreases oxidative DNA damage in human lymphocytes, Cancer Research, vol. 56, No. 6, 1996, pp. 1291-1295.

Chakraborty, Sutapa et al, Prevention and repair of DNA damage by selected phytochemicals as measured by single cell gel electrophoresis, Journal of Environmental Pathology Toxicology and Oncology, vol. 23, No. 3, 2004, pp. 215-226.

Silver, et al.; Effect of Antioxidant Intake on Sperm Chromatin Stability in Healthy Nonsmoking Men; J of Andrology, Jul./Aug. 2005, vol. 26, No. 4, 550-556.

King, et al.; In vivo antioxidant status, DNA damage, mutation and DNA repair capacity in cultured lymphocytes from healthy 75- to 80-year-old humans; Univ. of Ulster, Mutation Research 377 (1997) 137-147.

Duthie, et al.; The effects of cranberry juice consumption on antioxidant status and biomarkers relating to heart disease and cancer in healthy human volunteers; Eur J Nutr (2006) 45: 113-122.

Kazimirova, et al.; Does a vegetarian diet influence genomic stability?; Eur J Nutr (2004) 43: 32-38.

\* cited by examiner

*Observed trend (does not meet statically criteria)

n.s., not significant  * p = 0.007 [1-sample t-test] for change from baseline

DIETARY SUPPLEMENT AND RELATED METHOD

This is a continuation-in-part application of U.S. application Ser. No. 10/915,784, filed Aug. 11, 2004, which is a continuation-in-part application of U.S. application Ser. No. 10/360,789, filed May 7, 2002 (now U.S. Pat. No. 6,989,161), which is a continuation-in-part application of U.S. application Ser. No. 09/878,377, filed Jun. 12, 2001 (now U.S. Pat. No. 6,511,675), which claims benefit of U.S. Provisional Application No. 60/210,746, filed Jun. 12, 2000, all of which are hereby incorporated by reference.

BACKGROUND OF THE INVENTION

The present invention relates to a composition and method for correcting a dietary deficiency, including an inadequacy of phytochemicals, vitamins and minerals.

Many people fail to practice healthy eating habits, such as consuming an adequate quantity and variety of food to meet U.S. Recommended Dietary Allowances. Only 22% of the subjects of a National Cancer Institute Study consumed the recommended daily number of dietary servings of fruits and vegetables—despite the fact that the recommended dietary intake of fruits and vegetables is well-known. For example. *The California Daily Food Guide; Dietary Guidelines for California*, California Department of Health Services (1990) recommends that each person consume at least five to nine servings of fruit and vegetables per day, including one serving of a vitamin A-rich deep green or dark orange fruit or vegetable, and at least one serving of a vitamin C-rich fruit or vegetable. Additionally, it is well reported that each person should consume at least 3 servings per week of vegetable protein in the form of legumes, nuts, or seeds. Some researchers suggest that a target of 400 grams (13 ounces) of fruits and vegetables is a sensible goal for the optimal quantity to be consumed daily. In terms of variety, it is recommended that persons should eat at least three different colors of fruits and vegetables daily.

The benefits of consuming a sufficient amount and variety of fruits and vegetables are many. For example, consuming fruits and vegetables has been shown to reduce the risk of a variety of degenerative diseases. In a prospective cohort study of 41,837 postmenopausal women, the association of fruit and vegetable consumption with lung cancer risk was investigated. The researchers found that the risk of lung cancer was approximately halved when the consumption of fruits and vegetables increased from 24 or less servings to an excess of 48 servings per week. Similarly, the risk of lung cancer was approximately halved when the consumption of green leafy vegetables, including spinach and parsley sources, increased from one or fewer servings to six or more servings per week. Steinmetz, K. et al., "Vegetables, Fruit, and Lung Cancer in the Iowa Women's Health Study," *Cancer Res.* 53:536-43 (1993). Another study found that an increased intake of fresh tomatoes (a major source of lycopene) was associated with a pattern of protection for all sites of digestive tract cancer. Stahl, W. et al., "Lycopene: A Biologically Important Carotenoid for Humans?" *Arc. Biochem. Biophys.* 336:1-9 (1996).

In addition to fruits and vegetables, herbs also provide health benefits. For example, the herb, rosemary, contains antioxidants such as carnosol, which may play a preventive role in cholesterol oxidation. Likewise, the herb, basil is known for its antioxidant activity. Like fruits and vegetables, however, the dietary intake of beneficial herbs is unsatisfactory.

Further research has shown that the typical U.S. diet is lacking in phytochemicals. Phytochemicals generally refer to plant-derived compounds which, when taken daily in combination with vitamins and minerals, provide improved cardiovascular and bone health, an improved antioxidant profile, decreased free radical damage, and overall enhancement of the body's natural defense system.

The typical diet, especially the U.S. diet, includes an inadequate amount and variety of fruits, vegetables and herbs, as well as the phytochemicals and associated antioxidants present in these materials. A typical diet is similarly deficient in necessary vitamins and minerals associated with fruits and vegetables. Although conventional multivitamins can supplement western diets with needed vitamins and minerals, many of these multivitamins fail to provide phytochemicals that target free radicals in the body and thereby improve the antioxidant profile of the supplement.

SUMMARY OF THE INVENTION

The present invention provides a composition including a unique combination of fruit vegetable, and herb dehydrates, concentrates, or extracts; and optionally vitamins, minerals and specialty ingredients to correct a dietary deficiency of those materials.

The composition of the present invention provides substantial health benefits. For example, in one embodiment, it can support the health of people who consume a nutritionally deficient diet; improve antioxidant and nutrient status; replenish serum nutrient and phytochemical levels as a result of inadequate diets to levels associated with decreased risk of certain degenerative disease states; minimize free radical damage that occurs as a result of normal aging processes and exposure to environmental stresses; and/or improve the status of specific biomarkers indicative of optimal health, namely homocysteine, lipid byproducts, mineral status and glutathione peroxidase.

In a more specific embodiment, the composition of the present invention can provide β-carotene, α-lipoic acid, selenium, and vitamins C and E, which improve the antioxidant profile of a person. Increased levels of folic acid and vitamins E target and improve cardiovascular health. Calcium, magnesium, and vitamin D targets and improves bone health. B vitamins improve energy metabolism. The compositions according to the invention can provide 100% of the U.S. Recommended Daily Intake of all vitamins and most minerals. The composition also can provide a variety of phytochemicals to produce a diverse antioxidant profile.

In an even more specific embodiment, the composition can include a combination of fruit, vegetable and herbal ingredients, wherein the fruit ingredients are selected from acerola, apple, blueberry, citrus bioflavonoids, cranberry, grape skin, plum, and pomegranate; wherein the vegetable ingredients are selected from asparagus, alfalfa, brassica, kale, lutein, lycopene, and watercress; and wherein the herbal ingredients are selected from basil, oregano, parsley, sage and rosemary. These ingredients can be concentrated, for example they may be extracted from raw ingredients. Optionally, the fruit ingredients, vegetable ingredients and herbal ingredients can be present in the composition in a ratio of about 3.5:1:1 by weight. Specialty ingredients, such as alpha lipoic acid and inositol can be added to the composition.

In yet another embodiment, the composition can include at least one fruit ingredient selected from the group consisting of citrus bioflavonoids and pomegranate, and optionally at least one of acerola, apple, blueberry, cranberry, grape skin, plum and raspberry; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

In another embodiment, a method is provided for enhancing the immune system, as well as treating and/or reducing die risk of DMA damage of the human body comprising administering an effective amount of a composition including at least one fruit ingredient selected from the group consisting of citrus bioflavonoids and pomegranate, and optionally at least one of acerola, apple, blueberry, cranberry, grape skin, and plum; at least one vegetable ingredient selected from the group consisting of asparagus, lutein, lycopene, and watercress, and optionally at least one of alfalfa, brassica, and kale; and at least one herbal ingredient selected from the group consisting of basil, oregano and rosemary, and optionally at least one of parsley and sage.

These and other objects, advantages and features of the invention will be more readily understood and appreciated by reference to the detailed description of the invention and the drawings. It is to be understood that both the foregoing general description and the following detailed description are exemplary and explanatory only and are not restrictive of the invention as claimed.

DETAILED DESCRIPTION OF THE INVENTION

I. Overview

Figure 1:
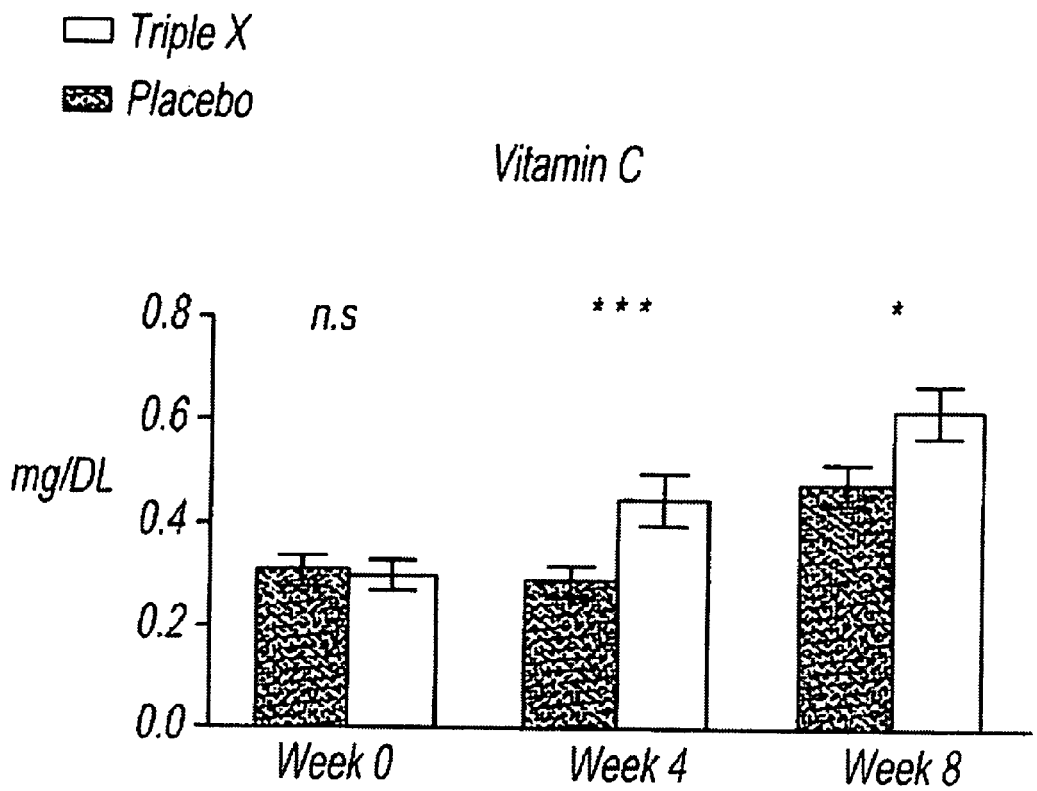
FIG. 1 is a graph depicting the effect the composition has on Vitamin C levels.
Figure 2:
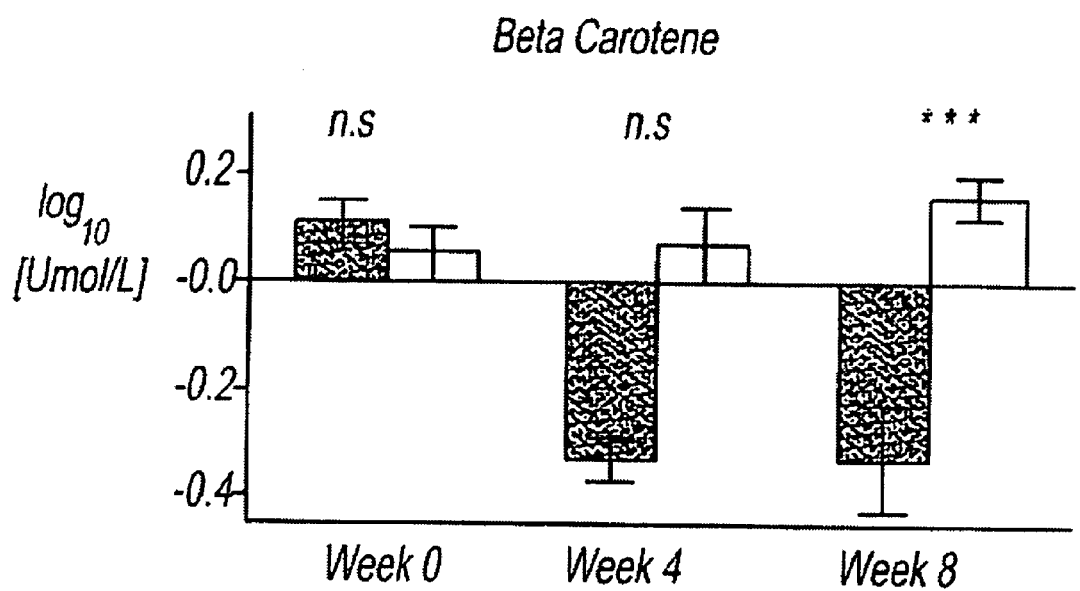
FIG. 2 is a graph depicting the effect the composition has on beta carotene levels.
Figure 3:
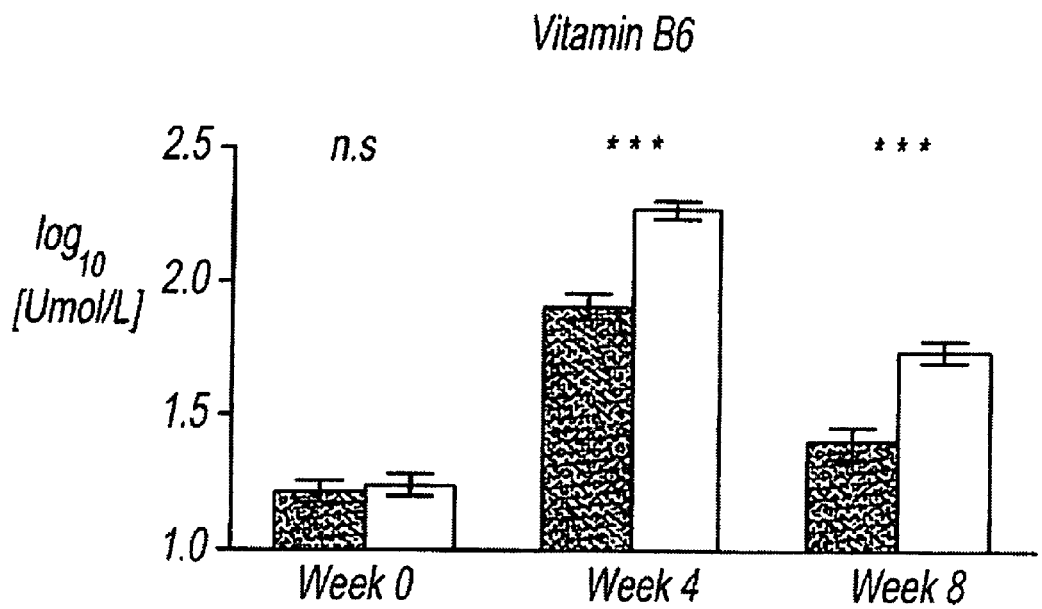
FIG. 3 is a graph depicting the effect the composition has on Vitamin $B_6$ levels.
Figure 4:
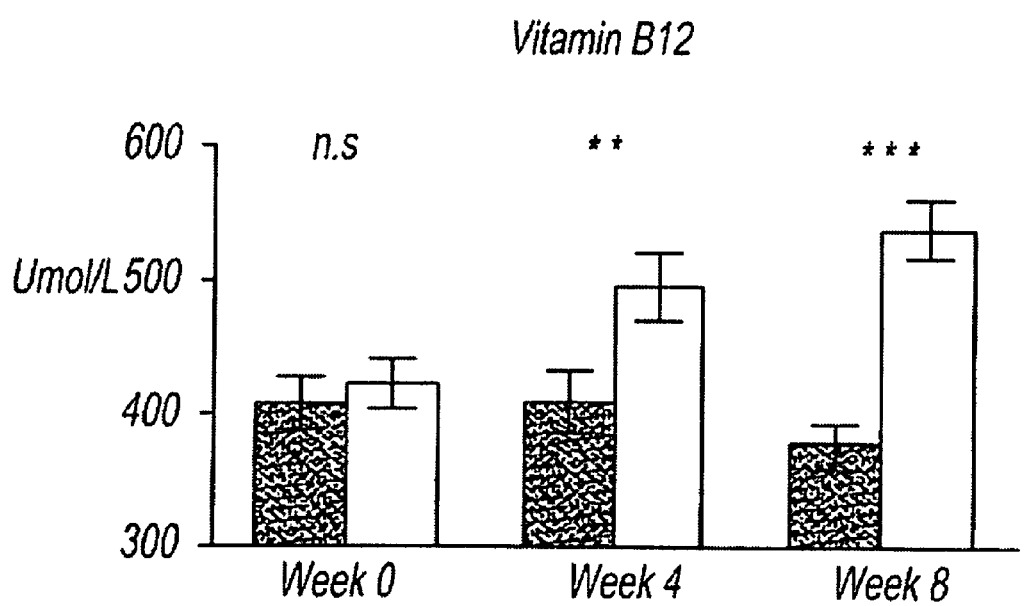
FIG. 4 is a graph depicting the effect the composition has on Vitamin $B_{12}$ levels.
Figure 5:
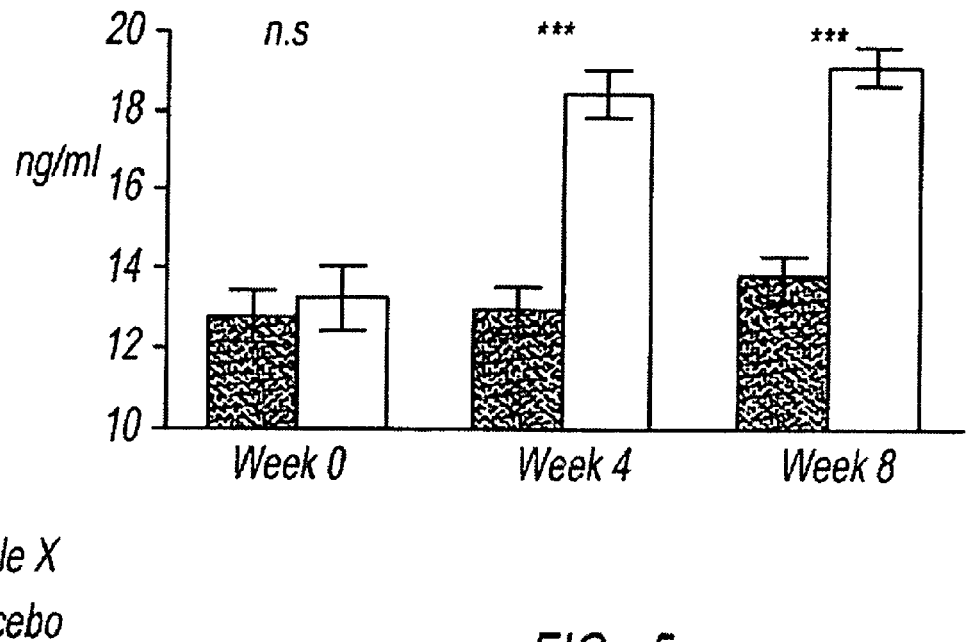
FIG. 5 is a graph depicting the effect the composition has on Folate levels.

In general, the invention relates to a composition comprising fruits, vegetables and herbs. In one embodiment, the composition can include a fruit ingredient, a vegetable ingredient and an herbal ingredient, wherein the fruit ingredient is at least one of pomegranate and citrus bioflavonoids, wherein the vegetable ingredient is at least one of asparagus, lutein, lycopene and watercress, and wherein the herbal ingredient is at least one of basil, oregano and rosemary. The composition can also be combined with a known therapy that can impact chromatin stability thereby limiting the detrimental effects of such therapy.

The following fruit ingredients also can be present in the composition: acerola, apple, blueberry, cranberry, grape skin, and plum. Further, the following vegetable ingredients also can be present in the composition: alfalfa, brassica, and kale. Finally, the following herbal ingredients also can be present in the composition: sage and parsley.

The composition has a synergistic effect in the treatments discussed herein. Thus, the components of the composition together are more effective that individually. Additionally, the composition modulates, and more specifically as discussed herein up-regulates, genes associated with chromatin stability, examples of which are discussed in the figures and examples.

Example of genes involved in telomere maintenance include, but are not limited to, Ku, Cdc 13 protein, the catalytic subunit EST2, and three other genes, EST1, EST3, EST4/CDC13, MRE11, RAD50, XRS2 (yeast)/NBS1, p53, hTERT, ATM, TRF2, the TERF family of genes.

The composition of the present invention can either treat or reduce the occurrences/risks of chromatin damage, and thus support genome stability, by increasing the expression of genes involved in identifying and correcting damage to DNA as well as associated protein structures (i.e., chromatin). The reduction in the occurrence/risk of chromatin damage includes any statistically significant reduction that correlates to a biological response or outcome. These genes control activities including, but not limited to, repair of base pair mismatches, repair of double strand breaks, or other maintenance, repair or supervisory roles. Most damage is caused by oxidation, nutrient deficiency, radiation or toxins. There are four main types of damage to DNA due to endogenous cellular processes or exogenous insult such as ultraviolet radiation: oxidation of bases [e.g. 8-oxo-7,8-dihydroguanine (8-oxoG)] and generation of DNA strand interruptions from reactive oxygen species, alkylation of bases (usually methylation), such as formation of 7-methylguanine, 1-methyladenine, O6 methylguanine hydrolysis of bases, such as deamination, depurination and depyrimidination, mismatch of bases, due to errors in DNA replication, in which the wrong DNA base is stitched into place in a newly forming DNA strand, or a DNA base is skipped over or mistakenly inserted. There are four major DNA-repair pathways in human cells: mismatch repair, nucleotide-excision repair (NER), base-excision repair (BER), and double-strand-break (DSB) repair. The NER pathway mainly removes bulky DNA adducts. The BER pathway is responsible for removal of oxidized DNA bases that may arise endogenously or from exogenous agents. The DSB pathway is responsible for repairing double-strand breaks caused by a variety of exposures, including ionizing radiation, free radicals, and telomere dysfunction. Examples of such genes include, but are not limited to ERCC, RAD2, RAD6, RAD7, RAD18, RAD23, RAD51, RAD54, CDC7, CDC8, CDC9, MAG1, PHR1, DIN1, DDR48, RNR1, RNR2, RNR3, UB14, repB, repD and APE. These genes are impacted by the composition of the present invention can modulate any of the types of damage disclosed above.

The composition can thus be used to treat diseases associated with DNA repair problems including, but not limited to, xeroderma pigmentosum, Cockayne syndrome, trichothiodystrophy, Werner's syndrome, Bloom's syndrome and ataxia telangiectasia. All of which are associated with improper repair of DNA.

The composition can also be used to affect/modulate the function of mitochondria function-specific genes, examples of such genes are provided in Table 8 below. These genes generally fall into four categories. First, genes for mitochondrial transcription/translation, examples of which include, but are not limited to, MTRF1L, which is involved in mitochondrial translational machinery, GFM2, which is a protein involved in protein elongation, MRPL3, which is a mitochondrial ribosomal protein, TOMM20, which is a central component of the receptor complex responsible for the recognition and translocation of cytosolically synthesized mitochondrial preproteins and together with TOM22 functions as the transit peptide receptor at the surface of the mitochondrion outer membrane and facilitates the movement of preproteins into the TOM40 translocation pore. COX15, which is predominantly found in tissues characterized by high rates of oxidative phosphorylation (OxPhos) involved in heme biosynthesis, POLG2, mtDNA that is replicated accurately by DNA polymerase gamma, and MRPS10, which is part of mitochondrial 28S Ribosomal protein. Second, genes for mitochondrial structure examples of such genes include, but are not limited to, DNMIL, which is critical for maintenance of mitochondrial morphology, OPA1, which is a major organizer of the mitochondria); inner membrane and is required for the maintenance of cristae integrity, MFN1, which is an essential transmembrane GTPase, which mediates mitochondrial fusion (MFN1 acts independently of the cytoskeleton.), BNIP3, which provides regulation of mitochondrial permeability, COX18, which is required for the insertion of integral membrane proteins into the mitochondrial inner membrane and is essential for the activity and assembly of cytochrome c oxidase and plays a central role in the translocation and export of the C-terminal part of the COX2 protein into the mitochondrial intermembrane space, and DNM1L, which functions in mitochondrial and peroxisomal division probably by regulating membrane fission and enzyme hydrolyzing GTP that oligomerizes to form ring-like structures and is able to remodel membranes. Third, miscellaneous mitochondrial proteins examples of such genes include, but are not limited to, WWOX, a tumor suppressor gene, PPIF, for protein folding, CoQ9, 10GB, which is involved in the final steps in the synthesis of CoQ, SLC25A37, which is a mitochondrial iron transporter that specifically mediates iron uptake in developing erythroid cells, thereby playing an essential role in heme biosynthesis, ABCB7, which is involved in the transport of heme from the mitochondria to the cytosol, and SLC25A36, which is a transporter for mitochondria. Fourth, genes for mitochondrial enzymes examples of such genes include, but are not limited to, SDHD, which is part of the respiratory chain, ATPAF1 enzymes which are critical for generation of ATP, NARS2, IARS2, EARS2, LARS2, HARS2, which are enzymes involved in the production of amino acid, ASN, ILE and GLN, LEU and HIS respectively, HIBADH, which is an enzyme providing succinyl coA for TCA cycle, ACADSB, which is an enzyme catalyzing one of the steps in fatty acid beta oxidation, MIB1, which is a E3 ligase necessary for protein ubiquitnation (deletion lethal), BCKDHB and ACAD8, for the generation of succiny Co A for TCA, AFG3L2, which is a AAA protease protecting against oxiative stress, PEO1, which is a DNA helicase, critical for lifetime maintenance of mtDNA integrity and to maintain mtDNA copy number, HK2 (Hexokinase 2), and HADHB, which is involved in fatty acid beta-oxidation.

The composition can also be combined with a known therapy to create a combinatorial therapy. This can primarily be used in instances where the known therapy has known detrimental side effects that impact DNA stability, such as chemotherapeutics and radiotherapeutics. Other compounds can also be used that negatively impact DNA repair and stability.

The invention also relates to a method for correcting a diet-induced deficiency of fruits, vegetables and herbs, and the nutrients present in such materials. The composition of the present invention additionally can contain phytochemicals, vitamins, and minerals known to improve the body's natural defenses against oxidants, free radicals, and diseases.

II. Composition and Method of Manufacture

The composition can include a combination of fruit, vegetable, herbal and other ingredients that provide significant health benefits. The following tables illustrate representative daily amounts of suitable fruits, vegetables, herbs, vitamins, and minerals which can be included in the composition. The dosages and methods of administration can be varied as desired from application to application. For example, Dosage A represents a range of dosages of the respective ingredients that is suitable for purposes of the present, invention. Dosage B represents a dosage of a particular embodiment. The unit "mg" in Tables 1-5 means that that the amount recited is given in the number of, e.g., milligrams, provided in a two-tablets per day dosage, unless otherwise noted, e.g., "JU" is recited. Thus, to determine the amount of a specific ingredient per single tablet, the amount recited in the respective tables must be halved.

TABLE 1

| Fruit Ingredient | Dosage A, mg/day | Dosage B, mg/day |
| --- | --- | --- |
| Acerola Powder | 50-500 | 300 |
| Apple extract | 25-1000 | 50 |
| Citrus Bioflavanoids | 25-1000 | 100 |
| Grape skin extract | 25-1000 | 50 |
| Plum extract | 25-1000 | 50 |
| Cranberry extract | 25-1000 | 50 |
| Pomagranate | 5-500 | 25 |
| Blueberry extract | 25-1000 | 50 |

The citrus bioflavonoids are commercially available from Access Business Group International LLC of Ada, Mich. This ingredient can be in a concentrate form, and can include, but are not limited to, naringen, hesperidin, narirutin, diosmin, rutin, tangeretin, diosmetin, neohesperidin, nobiletin, and quercetin.

TABLE 2

| Vegetable Ingredient | Dosage A, mg/day | Dosage B, mg/day |
| --- | --- | --- |
| Asparagus | 25-1000 | 50 |
| Alfalfa | 25-1000 | 70 |
| Brassica | 25-1000 | 50 |
| Kale | 20-1000 | 75 |
| Lycopene | 0.1-100 | 2 |
| Lutein esters | 0.1-100 | 2 |
| NUTRILITE Watercress | 5-500 | 28 |

NUTRILITE watercress is available from Access Business Group International LLC. The Brassica and/or kale can be in dehydrated, powdered form. As used herein the Brassica ingredient may include any material derived from plants in the Brassicae family, for example, broccoli. The lutein esters used in the composition can be of the type sold under the name Xangold 10% beadlets, which is available from Cognis Nutrition & Health of Cincinnati, Ohio. The lycopene used in the composition can be of the type sold under the name Lycobeads 5%, which is available from H. Reisman Corp. of Orange, N.J.

TABLE 3

| Vegetable Ingredient | Dosage A, mg/day | Dosage B, mg/day |
| --- | --- | --- |
| Basil extract | 25-1000 | 50 |
| Rosemary extract | 25-1000 | 50 |
| Sage | 5-500 | 25 |
| Oregano extract | 25-1000 | 50 |
| NUTRILITE Parsley | 5-500 | 25 |

NUTRILITE parsley is available from Access Business Group International LLC. The composition can also include ingredients in addition to the fruit, vegetable and herbal ingredients noted above. For example, suitable vitamins for use in the compositions and methods of the present invention can include, vitamin A, vitamin B1, vitamin B2, vitamin B6, vitamin B12, niacin/niacinamide, pantothenic acid, folic acid, biotin, choline, vitamin C, vitamin D, and vitamin E. Table 4 below includes a suitable vitamin profile.

TABLE 4

Vitamin Profile

| Ingredient | Dosage A, mg/day | Dosage B, mg/day |
| --- | --- | --- |
| Vitamin C from Acerola Powder | 20-100 | 60 |
| Ascorbic Acid (C) | 100-700 | 440 |
| Vitamin A from Beta Carotene | 1000-10,000 IU | 7500 IU |
| Biotin | 0.01-4 | 0.300 |
| Pantothenic Acid from Cal Pan Gran | 5-300 | 50 |
| Choline | 10-400 | 50 |
| Folic Acid | 0.01-10 | 0.8 |
| Inositol | 5-100 | 25 |
| Vitamin E | 10-5000 IU | 150 IU |
| Mixed Tocopherols | 5-300 | 50 |
| Niacin/Niacinamide | 5-300 | 40 |
| Pyridoxine (B6) | 10-100 | 15 |
| Riboflavin (B2) | 1-100 | 12.75 |
| Thiamine (B1) | 1-100 | 11.25 |
| Vitamin A from Acetate | 100-10,000 IU | 2500 IU |
| Vitamin B12 | 0.01-50 | 0.045 |
| Vitamin D3 | 10-2000 IU | 400 IU |
| Yeast, Standardized@ (source of 100% RDA Bs) | 5-350 | 60 |

In addition to the vitamins listed above, minerals for use in the compositions and methods of the present invention include, for example, boron, calcium, chromium, copper, iodine, magnesium, manganese, molybdenum, potassium, selenium, vanadium, and zinc. Other vitamins and minerals may also be used. Table 5 below includes a mineral profile suitable for the composition of the present invention.

TABLE 5

Mineral Profile

| Ingredient | Dosage A, mg/day | Dosage B, mg/day |
| --- | --- | --- |
| Calcium | 100-2000 | 750 |
| Chromium | 0.01-5 | 0.120 |
| Copper | 0.01-5 | 2 |
| Iodine | 0.001-5 | 0.15 |
| Magnesium | 10-1000 | 300 |
| Manganese | 1-20 | 5 |
| Molybdenum | 0.001-75 | 0.075 |
| Potassium | 5-300 | 80 |
| Selenium | 0.001-5 | 0.100 |
| Zinc | 1-50 | 15 |

With the ingredients of Tables 1-3, and optionally the ingredients of Tables 4-5, the composition of the present invention can provide a significant portion of, and in many cases exceed, the recommended daily requirement for a variety of vitamins and minerals. Tables 6 and 7 below illustrate the potency of the composition, when taken in the above daily amounts, in terms of percentages of the daily requirements for the listed vitamins and minerals.

TABLE 6

| Vitamin | Amount/Day | % Daily Value |
| --- | --- | --- |
| Vitamin A (75% as β-Carotene), IU | 10,000 | 200% |
| Vitamin C, mg | 500 | 833% |
| Vitamin D, IU | 400 | 100% |
| Vitamin E, IU | 150 | 500% |
| Niacin/Niacinamide, mg | 40 | 200% |
| Vitamin $B_6$, mg | 15 | 750% |
| Vitamin $B_{12}$, mcg | 45 | 750% |
| Folic Acid, mcg | 800 | 200% |
| Biotin, mcg | 300 | 100% |
| Pantothenic Acid, mg | 50 | 500% |

TABLE 7

| Minerals | Amount/Day | % Daily Value |
| --- | --- | --- |
| Calcium, mg | 750 | 75% |
| Magnesium, mg | 300 | 75% |
| Iodine, mcg | 150 | 100% |
| Potassium, mg | 80 | 2% |
| Copper, mg | 2 | 100% |
| Zinc, mg | 15 | 100% |
| Manganese, mg | 5 | 100% |
| Chromium, mcg | 120 | 100% |
| Selenium, mcg | 100 | 143% |
| Molybdenum, mcg | 75 | 100% |

Additional specialty ingredients which can be used in the composition include, for example, methyl sulfonyl methane (MSM), α-lipoic acid (10 mg/day), catechins, polyphenols, flavanoids, lycopene, lutein, yeast, inositol, and para-aminobenzoic acid (PABA).

The composition of the present invention can be formulated using any pharmaceutically acceptable form of respective fruit concentrates, vegetable concentrates, herb concentrates, phytochemicals, vitamins, minerals, and other nutrients, including their salts. The compositions can be formulated into tablets, powders, gels, or liquids (a tablet, for the purposes of the present invention and as used throughout the application disclosure, refers to any form of a solid oral dosage, including but not limited to tablets, caplets, capsules, powders, etc.). The compositions can be formulated as powders, for example, for mixing with consumable liquids such as milk, juice, water, or consumable gels or syrups for mixing into other liquids or foods. The compositions can also be formulated with other foods or liquids to provide pre-measured compositional foods, for example, single-serving bars. Flavorings, binders, protein, complex carbohydrates, and the like can be added as needed.

According to one aspect of the invention, the composition is administered as three separate tablets, all three of which are administered twice a day; however, the composition may be administered in other forms and unit dosages as desired.

The composition of the present invention will be illustrated by, but is not intended to be limited to, the following examples.

EXAMPLE 1

Three tablets may be prepared to provide a) fruit, vegetable and herbal ingredients, b) vitamins and c) minerals. The first tablet includes the fruit, vegetable and herbal ingredients of Tables 1-3. The amount of each ingredient in this first tablet is half of the amount listed in the Dosage B of the Tables, as the table-listed amount is the amount present in two such tablets. The first tablet may also include carriers and other tableting aids such as silicon dioxide, magnesium oxide, calcium carbonate, croscarmellose sodium, microcrystalline cellulose and magnesium stearate in amounts that may be varied for purposes well known to those of skill in the art.

The second tablet includes vitamins of Table 4. The amount of each ingredient in this second tablet is half of the amount listed in the Table, as the table-listed amount is the amount present in two such tablets. The second tablet may also include carriers and other tableting aids such as microcrystalline cellulose, calcium carbonate, croscarmellose sodium, magnesium stearate, and silicon dioxide.

The third tablet includes minerals of Table 5. The amount of each ingredient in this third tablet is half of the amount listed in the Table, as the table-listed amount is the amount present in two such tablets. The third tablet may also include carriers and other tableting aids such as microcrystalline cellulose, calcium carbonate, croscarmellose sodium, magnesium stearate, and silicon dioxide.

The three tablets, when administered twice a day, complete the gap in phytochemicals that is present in the typical diet.

EXAMPLE 2

The following examples relate to methods of preparing the above three tablets. The ingredients are the same as those referred to above in Tables 1-5. For purposes of the following examples, however, tablets including the fruit, vegetable and herbal ingredients from Tables 1-3 are referred to as "Tablet 1"; tablets including the vitamin ingredients from Table 4 are referred to as "Tablet 2"; and tablets including the mineral ingredients from Table 5 are referred to as "Tablet 3." It is noted that other methods for preparing the tablets and other suitable delivery vehicles can be used as desired.

Tablet 1

Mixed tocopherols, D-alpha-tocopherol (succinate), and silicon dioxide (NF fine powder) are passed through a SWECO separator equipped with a 20 mesh screen into a 100 cubic foot PK blender. The ingredients are blended for ten minutes. Magnesium oxide (D.C. heavy), Acerola concentrate, citrus bioflavonoids complex, plum extract, apple extract, rosemary extract, basil extract, grape skin extract, cranberry extract, kale powder, asparagus extract, blueberry extract, parsley dehydrate, oregano extract, sage extract, pomegranate extract, and inositol are passed through a SWECO separator equipped with a 20 mesh screen into a 100 cubic foot PK blender. The ingredients are blended for ten minutes.

Lycopene (5%), lutein ester (beadlets), mixed tocopherols, calcium carbonate (granular), croscarmellose sodium and microcrystalline cellulose (silicified) are passed through a SWECO separator equipped with a 20 mesh screen directly into a 100 cubic foot PK blender. The mixture is blended for ten minutes. Next, magnesium stearate (Kosher) is passed through a SWECO separator equipped with a 20 mesh screen directly into a 100 cubic foot PK blender. The ingredients are blended for an additional five minutes. The resulting mixture is discharged into totes or supersacks, and compressed into tablets.

Tablet 2

Acerola concentrate, microcrystalline cellulose (silicified) and alpha lipoic acid are passed through a SWECO separator equipped with a 20 mesh screen directly into a 100 cubic foot P.K. blender. The ingredients are blended for ten minutes. Next, the following ingredients are passed through a SWECO separator equipped with a 20 mesh screen directly into the 100 cubic foot PK blender: thiamine mononitrate (97%), riboflavin, niacinamide, biotin trituration (1%), vitamin B12 (1.1%), calcium pantothenate granular, folic acid, pyridoxine HCl (95%), and choline bitartrate. The ingredients are blended for ten minutes. Next, the following items are passed through a SWECO separator equipped with a 20 mesh screen directly into the 100 cubic foot PK blender; beta carotene (beadlets), vitamin D3 (beadlets), yeast (standardized) and vitamin A (acetate). The mixture is blended for an additional ten minutes.

Next, the following ingredients are passed through a SWECO separator equipped with a 20 mesh screen directly into the 1.00 cubic foot PK blender: ascorbic acid (97%), calcium carbonate (granular), croscarmellose sodium, d-alpha-tocopherol succinate, silicon dioxide (NF fine powder). The mixture is blended for an additional ten minutes.

Next, magnesium stearate (Kosher) is passed through a SWECO separator equipped with a 20 mesh screen directly into the 100 cubic foot PK blender. The mixture is blended for an additional five minutes. The resulting mixture is discharged into totes or supersacks, and compressed into tablets.

Tablet 3

Zinc amino acid chelate, mixed tocopherols and silicon dioxide (NF fine powder) are passed through a SWECO separator equipped with a 20 mesh screen into a 100 cubic foot PK blender. The ingredients are blended for ten minutes. Co-processed alfalfa concentrate/microcrystalline cellulose/calcium carbonate, selenium yeast, microcrystalline cellulose, copper amino acid chelate, manganese amino acid chelate, potassium iodide trituration, chromium amino acid chelate, molybdenum amino acid chelate, brassica dehydrate, watercress dehydrate and croscarmellose sodium are passed through a SWECO separator equipped with a 20 mesh screen directly into a 100 cubic foot PK blender. The ingredients are blended for ten minutes.

Potassium chloride, magnesium oxide (D.C. heavy) and calcium carbonate (granulation) are passed through a SWECO separator equipped with a 20 mesh screen directly into a 100 cubic foot PK blender. The ingredients are blended for ten minutes. Next, magnesium stearate (Kosher) is passed through a SWECO separator equipped with a 20 mesh screen directly into a 100 cubic foot PK blender. The ingredients are blended for an additional ten minutes. Next, magnesium stearate (Kosher) is passed through a SWECO separator equipped with a 20 mesh screen directly into the 100 cubic foot PK blender. The mixture is blended for an additional live minutes. The resulting mixture is discharged into totes or supersacks, and compressed into tablets.

EXAMPLE 3

Figure 7:
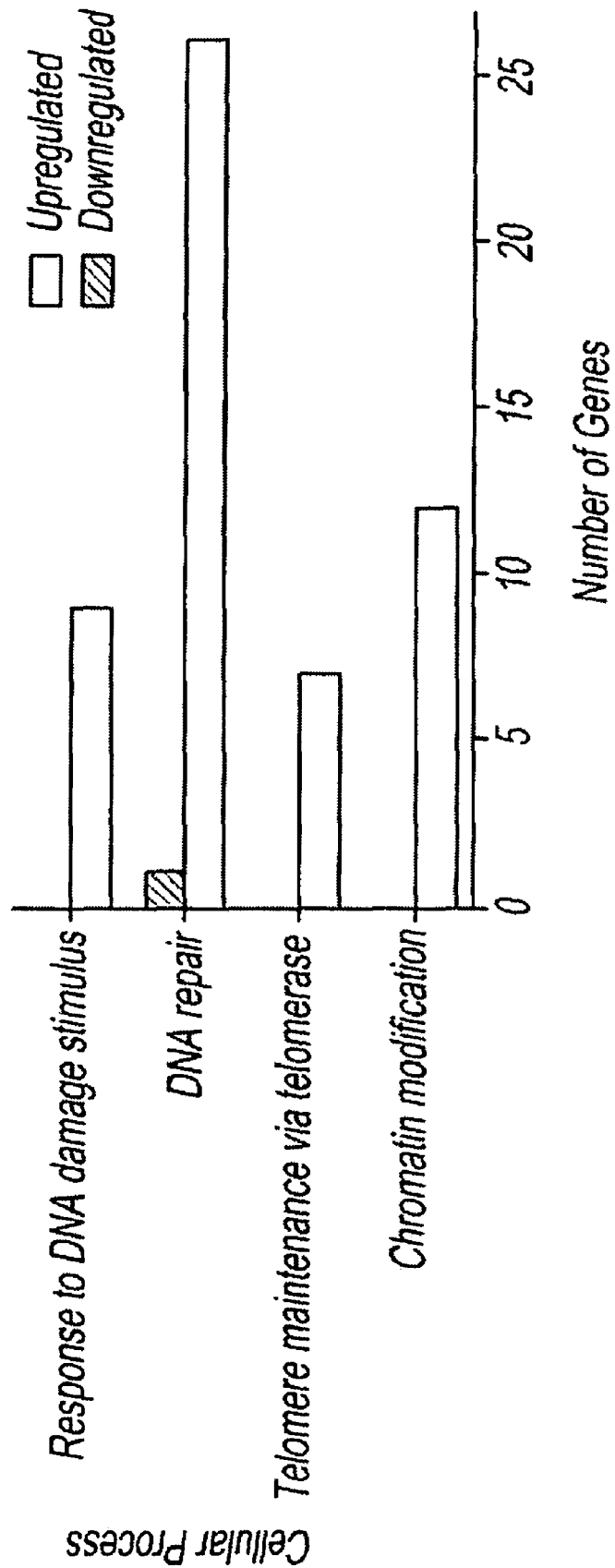
FIG. 7 is a graph depicting the numbers of genes related to DNA or chromatin maintenance or repair that were modulated by consumption of the composition.
Figure 8B:
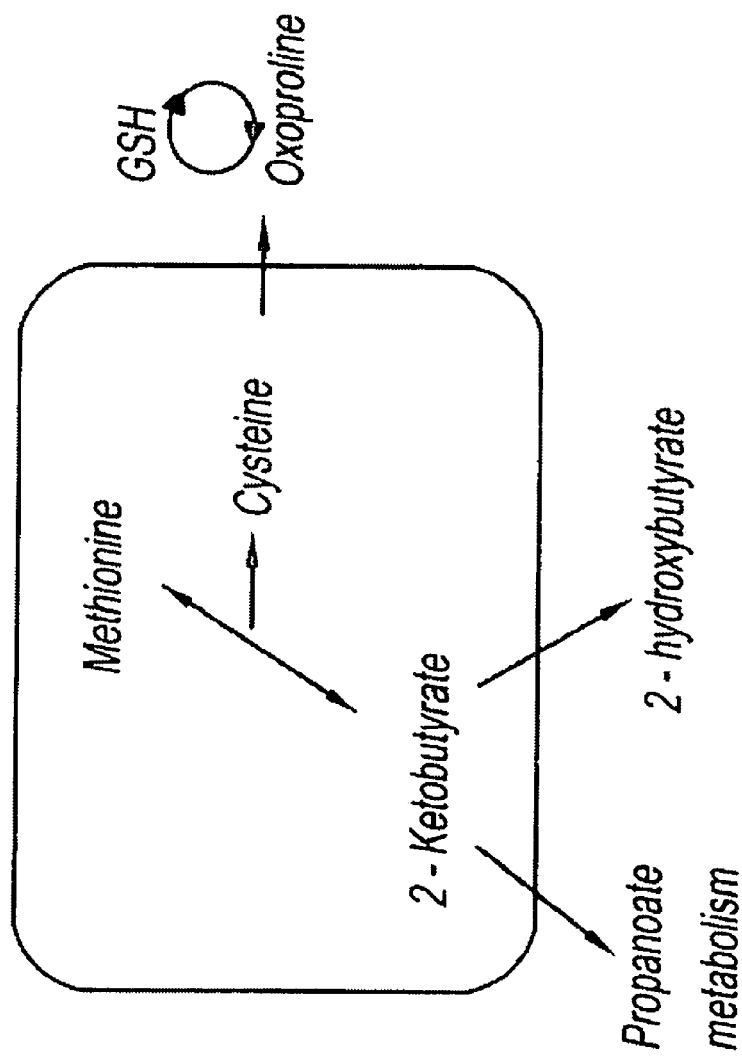
FIGS. 8A and 8B which are a diagram (FIG. 8A) and a graph (FIG. 8B) depicting decreased oxidative stress with treatment using the composition of the present invention as indicated by decreased concentration of 2-hydroxybutarate.
Figure 8A:
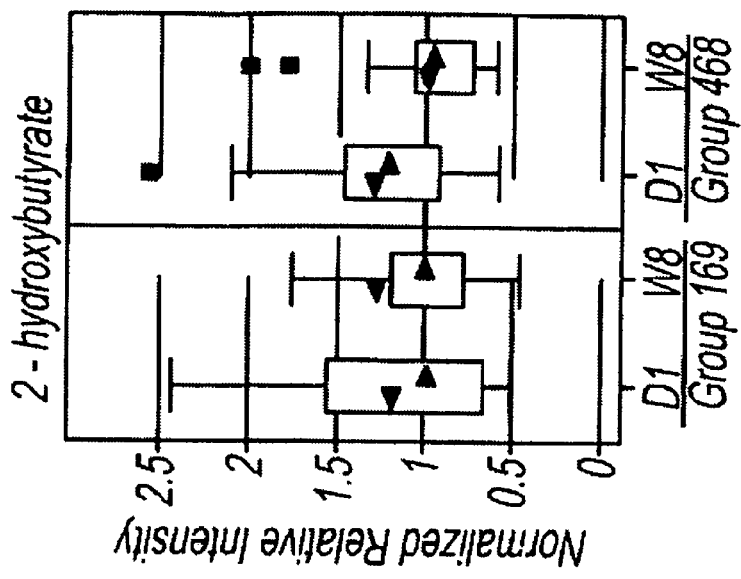
Figure 9B:
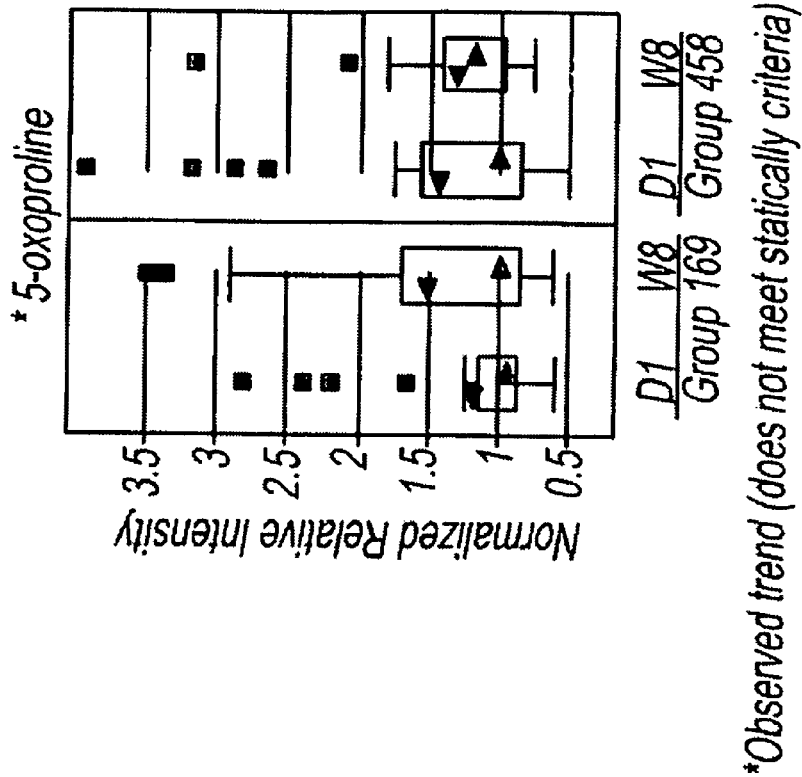
FIGS. 9A and 9B are a diagram (FIG. 9A) and a graph (FIG. 9B) depicting decreased oxidative stress with treatment using the composition of the present invention as indicated by decreased concentration of 5-oxoproline.
Figure 9A:
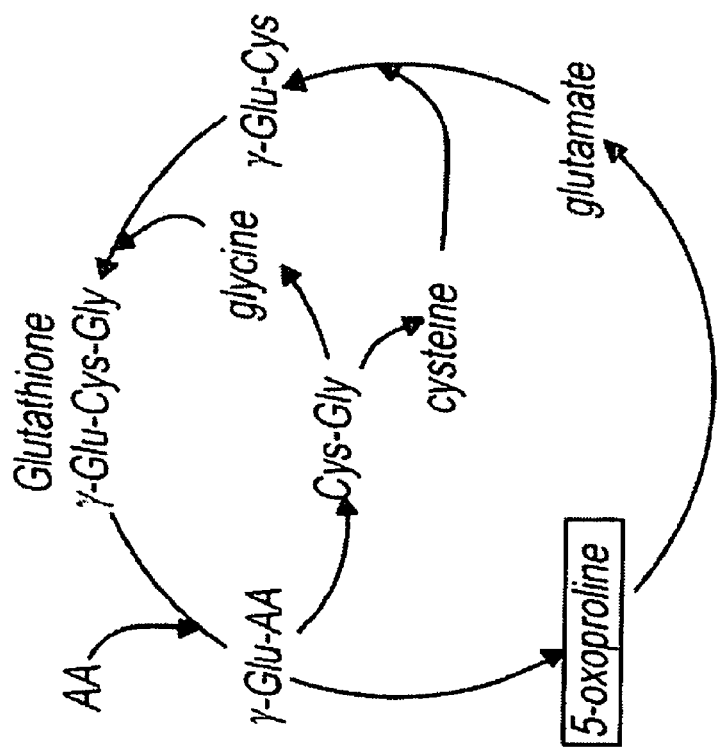
Figure 10:
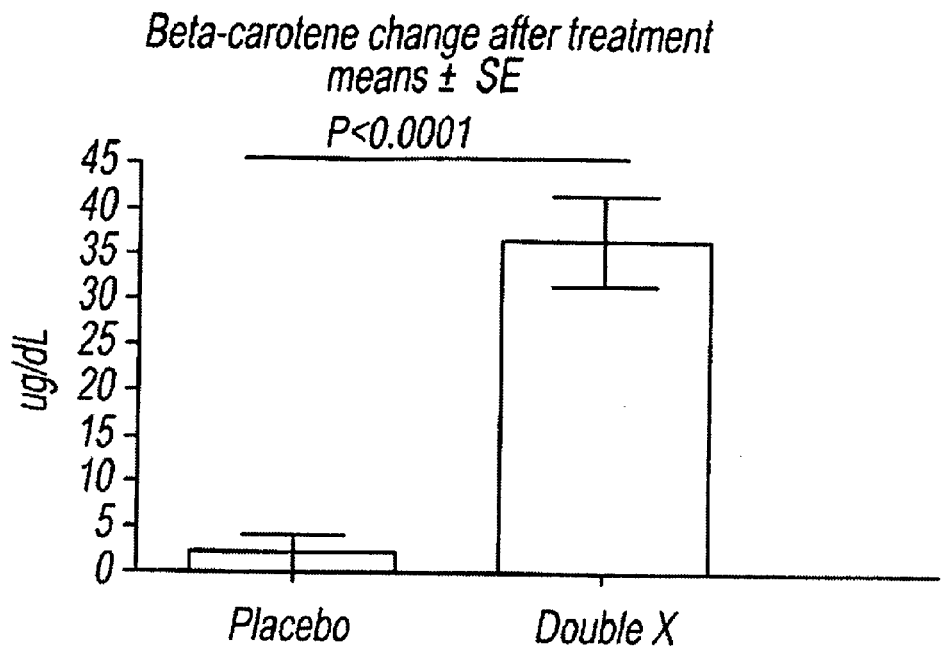
FIG. 10 is a graph depicting the change in plasma beta-carotene concentration after treatment.
Figure 11:
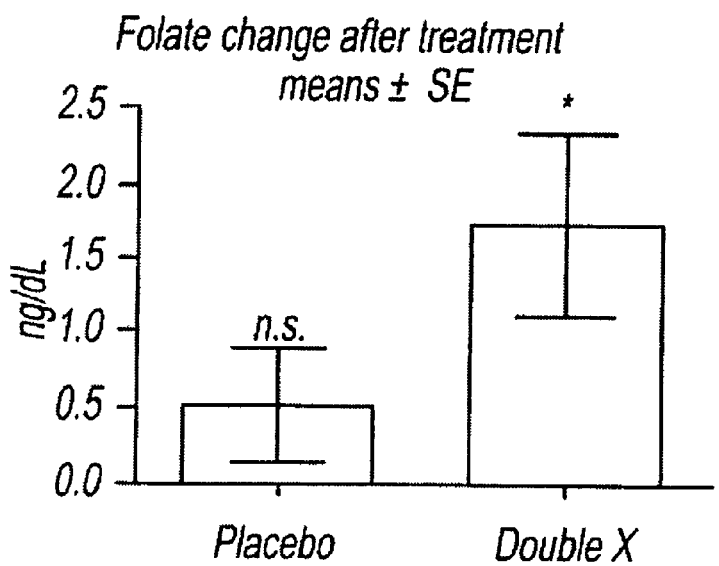
FIG. 11 is a graph depicting the change in plasma folate concentration after treatment.
Figure 12:
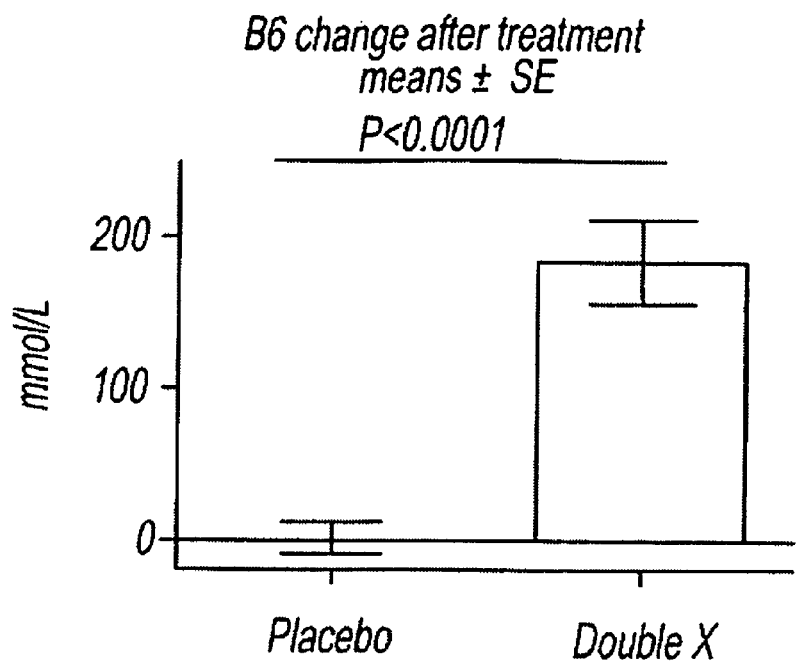
FIG. 12 is a graph depicting the change in plasma vitamin B6 concentration after treatment.
Figure 13:
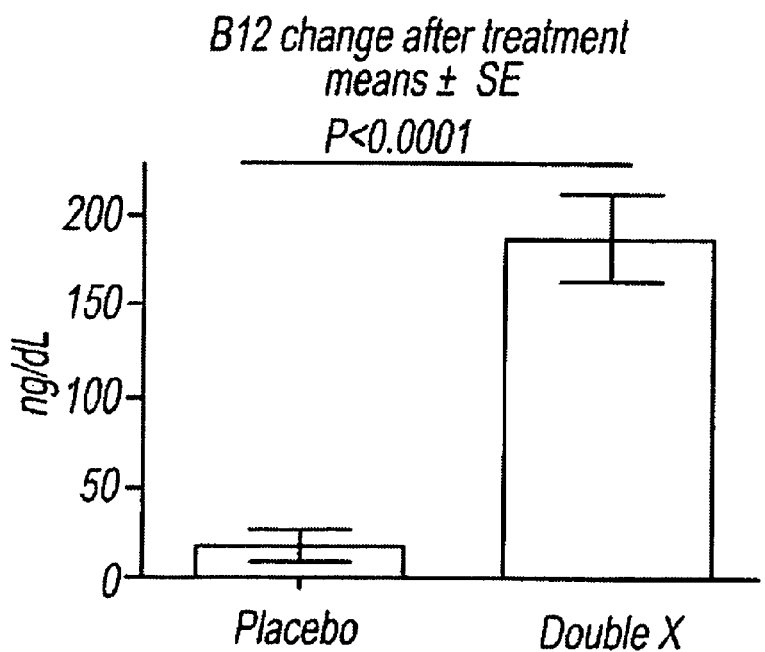
FIG. 13 is a graph depicting the change in plasma vitamin B12 concentration after treatment.
Figure 14:
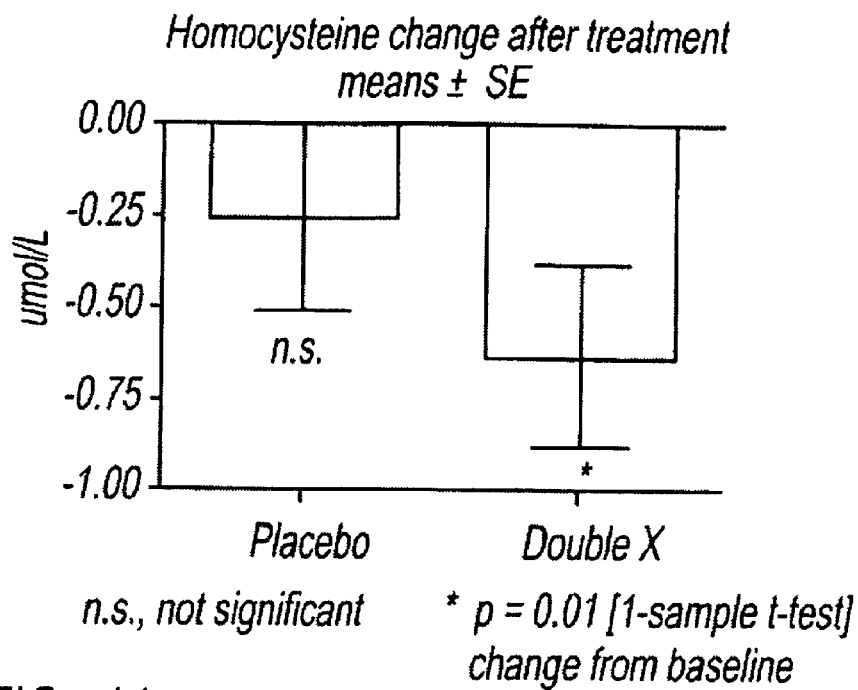
FIG. 14 is a graph depicting the change in plasma homocysteine concentration after treatment.
Figure 15:
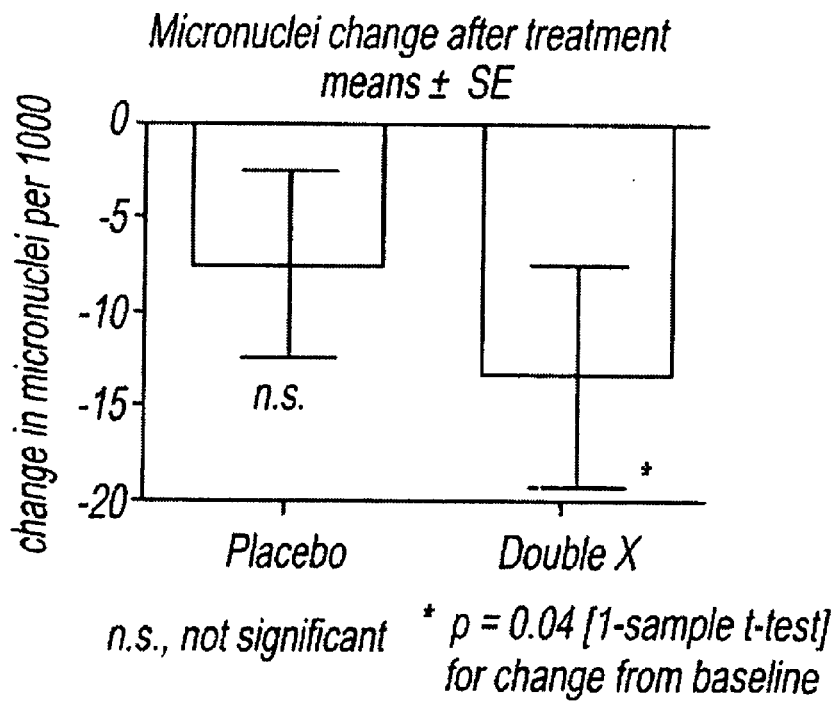
FIG. 15 is a graph depicting the change in DNA damage after treatment.
Figure 16:
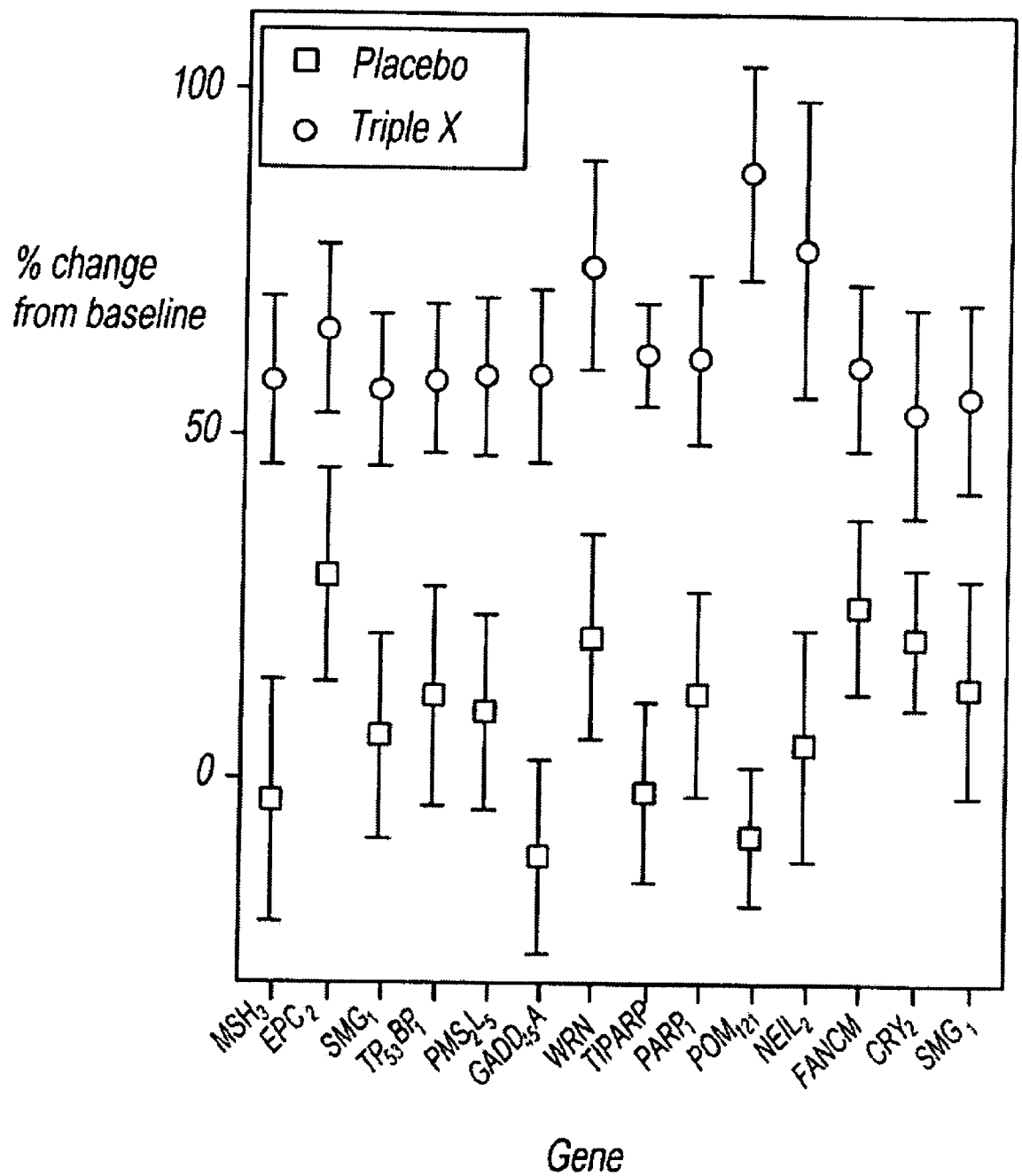
FIG. 16 is a graph depicting the change in baseline expression activity of genes associated with DNA maintenance genes after treatment.

The clinical study was an independent Review Board-approved, double-blind, placebo-controlled, parallel-groups study.
Subjects
Subjects were 120 healthy adult Japanese-Americans in California and Hawaii Subjects were ethnically Japanese (both parents and four grandparents ethnically Japanese) and ate a mostly Japanese diet
Treatment
Subjects took either composition or placebo as directed (12 tablets a day) for 8 weeks. The composition is the same formula as is currently marketed in Japan under the Alticor name of Triple X™. All products were coated and provided in coded foil packs to preserve double-blindedness.
Outcome Measures
There were four main categories of outcome measures; (1) plasma concentrations of a representative water-soluble antioxidant nutrient [vitamin c], and a representative fat-soluble antioxidant nutrient [beta carotene], (2) plasma concentrations of the "anti-homocysteine triad" vitamin B6, vitamin B12, and folate, as well as plasma concentrations of homocysteine, (3) nutrigenomic mechanisms of genomic stability, and (4) plasma metabolomic profile changes.
Analyses for plasma nutrient and homocysteine concentrations were based on blood samples obtained from 120 subjects (60 treated with Triple X, and 60 treated with Placebo), at baseline, Week 4, and Week 8.
Nutrigenomic analyses were based on blood samples obtained from 14 subjects (7 treated with Triple X, and 7 treated with Placebo) at baseline and Week 2.
Statistics
Plasma nutrient and homocysteine change score results were assessed with independent-groups t-test for between-groups comparisons. A P value smaller than 0.05 was considered significant.
Nutrigenomic data were first analyzed with paired t-tests within the composition-treated group only to identify which from among 44,000 genes measured showed a significant change in expression level following treatment. A P value smaller than 0.05 was considered significant. A Q value (false discovery rate) of 0.4 was used to control for false positive findings. This analysis identified about 2,000 genes, which were then examined for biologically relevant patterns of change.
Results from the clinical study were as follows. Compared to subjects taking Placebo, subjects taking composition showed increased levels of folate, vitamin B6, vitamin B12, and vitamin C, as well as decreased levels of homocysteine, all within 4 weeks of treatment, with results maintained at 8 weeks. Metabolomic analyses indicate decreased oxidative stress. Nutrigenomic analyses indicate increased genomic integrity and tumor suppressor mechanisms, homocysteine metabolism, resistance to oxidative stress and lipid peroxidation.
Clinical interpretation of nutrigenomic data revealed the unexpected finding that about 150 genes, each known to function to support genomic stability (via chromatin maintenance, damage detection, and repair), were significantly increased in the Triple X group compared to the placebo group. Subsequent analysis of these genes in the Placebo-treated group showed no change following Placebo treatment. Compared to baseline, consumption of the composition of the present invention led to statistically significant increases in the expression of genes related to DNA maintenance, replication, or repair (FIG. 7).
Clinical interpretation of metabolomic data revealed the unexpected findings that consumption of Triple X led to significant decrease increases in 2-hydroxy bury rate, a metabolite related to oxidative stress (FIG. 9), as well as a trend towards a decrease in 5-oxoproline, also a metabolite related to oxidative stress (FIG. 10). This shows that the consumption of the composition can lead to increased plasma concentration of antioxidant nutrients, increased expression of chromatin maintenance and repair genes, decreased homocysteine, and decreased metabolomic indicators of oxidative stress.

EXAMPLE 4

Clinical testing was conducted to confirm the efficacy of the composition of the present invention. It was expected that consumption of the composition would: correct dietary deficiencies of phytochemicals; improve the amount of antioxidants in the body; decrease free radical damage; increase plasma vitamin, mineral and phytochemical concentrations; and improve plasma and systemic antioxidant capacity, among other things.

Inclusion criteria for this study were healthy men and women, from 18 to 80 years of age, who consume fewer than 12 items found on the Recommended Foods Checklist per week. These subjects are selected after administration of a food frequency questionnaire and application of the Recommended Foods Score (RFS). The RFS consists of 23 foods, 14 of which are fruits and vegetables, that when consumed on a weekly basis have been associated with reduced mortality. This was demonstrated in a cohort study of 42,254 women. Those with a mean RFS of 16.0 (highest quartile) had an all-cause mortality relative risk of 0.69 compared to those with a mean RFS of 6.4 (lowest quartile) who have an all-cause mortality relative risk. It was noted that those in the highest quartile consumed significantly more calories (131%), fiber (200%), Vitamin C (230%), folate (181%), and pro-Vitamin A carotenoids (253%) compared to those in the lowest quartile.

The clinical study encompassed a double-blind (i.e. to subjects and investigators) study of 120 subjects over a six-week period. During the six-week trial, subjects were told to consume three tablets, either the composition, or a placebo, twice a day, such as morning and evening. The subjects were tested by taking blood and urine samples and performing the following assays: total polyphenols, plasma ORAC (Oxygen Radical Absorption Capacity), CP450 enzyme induction, cytokinesis block micronucleus assay, comet assay, bioenergetics assay, urinary bile acids, B6, B12, folate, Vitamin C, homocysteine, alpha and gama tocopherols, beta-carotene, C-reactive protein and urinary 8-epi prostaglandins F2α, which were tested at baseline, two weeks, four weeks and six weeks into the study. Improvement, and thus, efficacy of the composition, was measured based on: plasma concentrations of vitamins, minerals and phytochemicals; plasma and systemic antioxidant capacity; detoxification capacity; cellular energy dynamics; genomic stability; other risk factors and subjective effects.

It was expected that the results of the study would show that following six weeks of composition consumption, subjects would have significantly increased plasma levels of alpha tocopherols, B12, B6, folate, Vitamin C, and other antioxidants, which indicates an improvement in the amount of antioxidants in the body and which is associated with a correction of dietary deficiencies in vitamins, nutrients and phytochemicals, and/or a decrease in free radical damage, as well as increased genomic stability (i.e., decreased DNA damage) among other things.

Results from the clinical study were as follows. Compared to subjects taking Placebo, subjects taking the composition showed increased plasma concentrations of Beta Carotene, Alpha-Tocopherol, Folate, and Vitamins B6 and B12. Subjects taking composition also showed significantly reduced homocysteine, as well as decreased DNA damage as indicated by the cytokinesis micronucleus block assay. This shows that the consumption of the composition can increase plasma concentrations of antioxidant nutrients, decrease homocysteine, and decrease DNA damage.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

TABLE 8

| | | | | |
|---|---|---|---|---|
| ADH5 | \alcohol dehydrogenase 5 (class III), chi polypeptide\"" | Removal of S-nitrosoglutathione and thus controls its levels as well as levels of nitrosylated proteins. Protects against nitrosative stress. Low amounts of this enzyme or absence can increase whole cell nitrosylation and tissue damage and susceptibility to bacteria. | Anti-Nitrosative stress activity gene | |
| TXNL1 | thioredoxin-like 1 | TXNL1 acts as an effector of oxidants or a redox sensor | Anti-oxidant activity gene | |
| TXNRD3 | thioredoxin reductase 3 | Thioredoxin reductases (EC 1.6.4.5), such as TXNRD3, are selenocysteine (sec)-containing flavoenzymes that maintain thioredoxins, small proteins that catalyze redox reactions, in the reduced state using the reducing power of NADPH, sec residue of TXNRD1 serves as a sensor of reactive oxygen species. | Anti-oxidant activity gene | |
| UHRF2 | \ubiquitin-like, containing PHD and RING finger domains, 2\"" | Absence of this gene makes cells more sensitive to X rays, UV light and hydroxyurea | Anti-oxidant activity gene | |
| VPS8 | vacuolar protein sorting 8 homolog (S. cerevisiae) | VPS3, VPS8 and PEP7 genes to rescue lethal effects of oxidative damage resulted from the overexpression of these genes. | Anti-oxidant activity gene | |
| PAFAH2 | \platelet-activating factor acetylhydrolase 2, 40 kDa\"" | Membrane phospholipids are susceptible to oxidation, which is involved in various pathological processes such as inflammation, atherogenesis, neurodegeneration, and aging. One enzyme that may help to remove oxidized phospholipids from cells is intracellular type II platelet-activating factor acetylhydrolase (PAF-AH (II)), which hydrolyzes oxidatively fragmented fatty acyl chains attached to phospholipids. Overexpression of PAF-AH (II) in cells or tissues was previously shown to suppress oxidative stress-induced cell death. | Anti-oxidant activity gene | Detoxification activity gene |
| ME2 | \malic enzyme 2, NAD(+)-dependent, mitochondrial\ "" | The primary role of malic enzyme, however, may be to generate reduced NADP+ for biosynthesis rather than to form an intermediate of carbohydrate catabolism. NADPH provides the reducing equivalents for biosynthetic reactions and for oxidation-reduction involved in protection against the toxicity of ROS | Anti-oxidant activity gene | |
| PON2 | paraoxonase 2 | The encoded protein is ubiquitously expressed in human tissues, membrane-bound, and may act as a cellular antioxidant, protecting cells from oxidative stress. Hydrolytic activity against acylhomoserine lactones, important bacterial quorum-sensing mediators, suggests the encoded protein may also play a role in defense responses to pathogenic bacteria. | Anti-oxidant activity gene | |

TABLE 8-continued

| | | | |
|---|---|---|---|
| IVNS1ABP | influenza virus NS1A binding protein | Protects cells from cell death induced by actin destabilization; Protects neurons from dendritic spines and actin filaments damage induced by the actin-destabilizing cytochalasin B when overexpressed. May be a component of the cellular splicing machinery with a role in pre-mRNA splicing; may mediate the inhibition of splicing by NS/influenza virus NS1A protein. Highly present in neutrophil | Anti-viral |
| ILF3 | \interleukin enhancer binding factor 3, 90 kDa\"" | Nuclear factor of activated T-cells (NFAT) is a transcription factor required for T-cell expression of interleukin 2. NFAT binds to a sequence in the IL2 enhancer known as the antigen receptor response element 2. In addition, NFAT can bind RNA and is an essential component for encapsidation and protein priming of hepatitis B viral polymerase. NFAT is a heterodimer of 45 kDa and 90 kDa proteins, the larger of which is the product of this gene. The encoded protein, which is primarily localized to ribosomes, probably regulates transcription at the level of mRNA elongation, required for IL2 mRNA stabilization. Anti-viral activity | Anti-viral activity gene |
| SRPK2 | SFRS protein kinase 2 | SRPK1 and SRPK2 in HBV replication and found that both of them could suppress HBV replication by reducing the packaging efficiency of the pgRNA without affecting the formation of the viral core particles. | Anti-viral activity gene |
| PTX3 | \pentraxin-related gene, rapidly induced by IL-1 beta\"" | anti-viral activity | Anti-viral activity gene |
| RIPK2 | receptor-interacting serine-threonine kinase 2 | Anti-viral response | Anti-viral activity gene |
| SMARCE1 | \SWI/SNF related, matrix associated, actin dependent regulator of chromatin, subfamily e, member 1\"" | Suppression of hepatitis B virus (HBV) replication, a causative agent for chronic hepatitis, is an effective approach to controlling disease progression. Host factors have a significant effect on viral replication efficiency and need to be better characterized.. Cellular transcription modulator SMARCE1 binds to HBV core promoter containing naturally occurring deletions and represses viral replication. Transcriptional coactivator cooperating with nuclear hormone receptors to potentiate transcriptional activation, he SWI/SNF chromatin remodeling complexes are evolutionarily conserved multimeric enzymatic machines that alter the nucleosomal structure using energy derived from ATP hydrolysis (34). Ample experimental evidence suggests that the SWI/SNF complexes play important roles in fundamental cellular processes such as transcription, replication, and the repair of chromatin | Anti-viral activity gene |
| TLR7 | toll-like receptor 7 | TLR7-specific agonists activate plasmacytoid DCs (pDCs) and B cells and induce mainly IFN-a and IFN-regulated cytokines, the natural ligands of TLR7 and TLR8 were identified as single-stranded RNA (ssRNA), single stranded (ss)RNA viruses [either vesicular stomatitis virus (VSV; a rhabdovirus) or influenza virus (an orthomyxovirus)] stimulate type I IFN responses through TLR7. | Anti-viral activity gene |

TABLE 8-continued

| | | | |
|---|---|---|---|
| ZNF175 | zinc finger protein 175 | OTK18 was copiously expressed in macrophages following HIV type I infection and diminished progeny virion production. A mechanism for this antiretroviral activity was by suppression of HIV type 1 Tat-induced viral long terminal repeat promoter activity. | Anti-viral activity gene |
| BNIP2 | BCL2/adenovirus E1B 19 kDa interacting protein 2 | Adenovirus E1B 19-kD protein protects against cell death induced by viral infection and certain external stimuli. | Anti-viral activity gene |
| CDKN1A | \cyclin-dependent kinase inhibitor 1A (p21, Cip1)\"" | is an endogenous cellular component in stem cells that provides a molecular barrier to HIV-1 infection., anti-viral | Anti-viral activity gene |
| CREBZF | CREB/ATF bZIP transcription factor | The neuronal host cell factor-binding protein Zhangfei inhibits herpes simplex virus replication. | Anti-viral activity gene |
| ELF1 | E74-like factor 1 (ets domain transcription factor) | ELF-1 belongs to a subset of Ets factors that regulate vascular-specific gene expression during blood vessel development. | Blood vessel development gene |
| NUS1 | nuclear undecaprenyl pyrophosphate synthase 1 homolog (S. cerevisiae) | Acts as a specific receptor for the N-terminus of Nogo-B, a neural and cardiovascular regulator. Able to regulate vascular remodeling and angiogenesis. Its similarity with UPP synthetase proteins suggests that it may act as a scaffold for the binding of isoprenyl lipids and/or prenylated proteins. Nogo-B receptor localizes with the ligand Nogo-B during VEGF and wound healing angiogenesis in vivo, mediates chemotaxis in a heterologous expression system and chemotaxis, and 3D tube formation in native endothelial cells. Thus, identification of this receptor may lead to the discovery of agonists or antagonists of this pathway to regulate vascular remodeling and angiogenesis. | Blood vessel development gene |
| CLIC4 | chloride intracellular channel 4 | CLIC4 is involved in formation of the blood vessel lumen. Blood vessel formation. Chloride channel or a regulator or accessory subunit of other proteins that could provide the pore-forming function. | Blood vessel development gene |
| SGPP1 | sphingosine-1-phosphate phosphatase 1 | Sphingosine-1-phosphate (S1P) is a highly bioactive lipid that exerts numerous biological effects both intracellularly as a second messenger and extracellularly by binding to its G-protein-coupled receptors of the endothelial differentiation gene family (S1P receptors-(1-5)). Intracellularly, at least two enzymes, sphingosine kinase and S1P phosphatase, regulate the activity of S1P by governing the phosphorylation status of S1P. It is now well established that S1P is the natural ligand for specific G protein-coupled receptors (GPCRs), hereafter referred to as S1PRs. To date, five members, EDG-1/S1P1, vascular smooth muscle cells and pericytes to migrate around arteries and capillaries and properly reinforce them.angiogenesis. | Blood vessel development gene |
| DMTF1 | cyclin D binding myb-like transcription factor 1 | DMP1 is a pivotal tumor suppressor for both human and murine lung cancers. DMP1 is essential for normal postnatal chondrogenesis and subsequent osteogenesis-bone | Bone health |
| LEMD3 | LEM domain containing 3 | LEMD3 is involved in both BMP (see 112264) and TGF-beta (190180) signaling. an integral protein of the inner nuclear membrane, binds Smad2 and Smad3 and antagonizes transforming growth factor-beta signaling. Involved in multiple bone disorders. | Bone Health Activity Gene |

TABLE 8-continued

| Gene | Name | Description | Category |
|---|---|---|---|
| MBTPS1 | \membrane-bound transcription factor peptidase, site 1\"" | Site-1 protease (S1P) has an essential function in the conversion of latent, membrane-bound transcription factors to their free, active form. In mammals, abundant expression of S1P in chondrocytes suggests an involvement in chondrocyte function. Catalyzes the first step in the proteolytic activation of the sterol regulatory element-binding proteins (SREBPs). Other known substrates are BDNF and ATF6. | Bone Health Activity Gene |
| RPS6KA3 | \ribosomal protein S6 kinase, 90 kDa, polypeptide 3\"" | Rsk2 plays an important role in neuronal plasticity. RSK2 is required for osteoblast differentiation and function. Rsk2-null mice develop progressive osteopenia due to impaired osteoblast function and normal osteoclast differentiation. | Bone Health Activity Gene |
| BCAT1 | \branched chain aminotransferase 1, cytosolic\"" | This gene encodes the cytosolic form of the enzyme branched-chain amino acid transaminase. This enzyme catalyzes the reversible transamination of branched-chain alpha-keto acids to branched-chain L-amino acids essential for cell growth. | Cell health Maintenance Gene |
| CEPT1 | choline/ethanolamine phosphotransferase 1 | Cholinephosphotransferase catalyses the final step in the synthesis of phosphatidylcholine by the transfer of phosphocholine from CDP-choline to diacylglycerol. The synthesis of phosphatidylethanolamine by ethanolaminephosphotransferase occurs using an analogous reaction. This gene codes for a choline/ethanolaminephosphotransferase. The protein can synthesize either choline- or ethanolamine-containing phospholipids. Phosphatidylcholine is a class of phospholipids called "essential phospholipids | Cell health Maintenance Gene |
| DSCR1 | Down syndrome critical region gene 1 | The DSCR1 (Adapt78) gene is transiently induced by stresses to temporarily protect cells against further potentially lethal challenges. | Cell health Maintenance Gene |
| PAPOLA | poly(A) polymerase alpha | Polymerase that creates the 3' poly(A) tail of mRNA's. Also required for the endoribonucleolytic cleavage reaction at some polyadenylation sites. | Cell health Maintenance Gene |
| HSBP1 | heat shock factor binding protein 1 | exert cytoprotection and anti-apoptotic effects | Cell health Maintenance Gene |
| METAP1 | methionyl aminopeptidase 1 | Protein synthesis is initiated with a methionine residue in eukaryotic cells or a formylated methionine in prokaryotes, mitochondria, and chloroplasts. For a large subset of proteins, the initiator methionine is cotranslationally removed before further posttranslational modification. The proteolytic removal of N-terminal methionine is catalyzed by a family of enzymes known as methionine aminopeptidases (MetAPs). | Cell health Maintenance Gene |
| SGMS1 | sphingomyelin synthase 1 | Suppresses BAX-mediated apoptosis and also prevents cell death in response to stimuli such as hydrogen peroxide, osmotic stress, elevated temperature and exogenously supplied sphingolipids. May protect against cell death by reversing the stress-inducible increase in levels of proapoptotic ceramide. Required for cell growth | Cell health Maintenance Gene |
| STK39 | \serine threonine kinase 39 (STE20/SPS1 homolog, yeast)\"" | STE20 kinases involved in the regulation of ion homoeostasis and volume control in mammalian cells | Cell health Maintenance Gene |

TABLE 8-continued

| | | | |
|---|---|---|---|
| VCL | vinculin | Involved in cell adhesion. May be involved in the attachment of the actin-based microfilaments to the plasma membrane. May also play important roles in cell morphology and locomotion. | Cell health Maintenance Gene |
| XPNPEP1 | \X-prolyl aminopeptidase (aminopeptidase P) 1, soluble\"" | prolyl aminopeptidase (EC 3.4.11.9) is a proline-specific metalloaminopeptidase that specifically catalyzes the removal of any unsubstituted N-terminal amino acid that is adjacent to a penultimate proline residue. Because of its specificity toward proline, it has been suggested that X-prolyl aminopeptidase is important in the maturation and degradation of peptide hormones, neuropeptides, and tachykinins, as well as in the digestion of otherwise resistant dietary protein fragments, thereby complementing the pancreatic peptidases. Deficiency of X-prolyl aminopeptidase results in excretion of large amounts of imino-oligopeptides in urine | Cell health Maintenance Gene |
| NCAPD3 | \non-SMC condensin II complex, subunit D3\"" | Regulatory subunit of the condensin II complex, a complex which establishes mitotic chromosome architecture and is involved in physical rigidity of the chromatid axis. | Chomatin stability |
| AOF2 | amine oxidase (flavin containing) domain 2 | a family of multiprotein corepressor complexes that function through modifying chromatin structure to keep genes silent. The polypeptide composition of these complexes includes a common core of 2 subunits, HDAC1 (601241)/HDAC2 (605164) and the FAD-binding protein AOF2. functions as a histone demethylase and transcriptional corepressor, histone lysine-specific demethylase LSD1 interacts with p53 (191170) to repress p53-mediated transcriptional activation, and to inhibit the role of p53 in promoting apoptosis. | Chromatin modification |
| HMGN1 | high-mobility group nucleosome binding domain 1 | HMGN1 enhances the rate of heat shock-induced chromatin remodeling in the HSP70 promoter, thereby leading to an increase in the levels of HSP70 transcripts during the early stages of heat shock induction. | Chromatin modification |
| INOC1 | INO80 complex homolog 1 (*S. cerevisiae*) | INOC1 defines a subfamily of SWI2/SNF2 chromatin remodeling proteins. INOC1 displayed ATPase activity specific to double-stranded DNA and exhibited activity on isolated human mononucleosomes. ATP hydrolysis of double-stranded DNA occurred in a linear time course with a calculated Km of 167 microM, similar to that of other ATPases of the SNF2/SWI2 family. | Chromatin modification |
| PCAF | p300/CBP-associated factor | Histone acetyltransferase; Functions as a histone acetyltransferase (HAT) to promote transcriptional activation. Has significant histone acetyltransferase activity with core histones (H3 and H4), and also with nucleosome core particles. | Chromatin modification |
| RBBP4 | retinoblastoma binding protein 4 | Core histone-binding subunit that may target chromatin remodeling factors, histone acetyltransferases and histone deacetylases to their histone substrates in a manner that is regulated by nucleosomal DNA. Component of several complexes which regulate chromatin metabolism. | Chromatin modification |
| RCBTB1 | regulator of chromosome condensation (RCC1) and BTB (POZ) domain containing protein 1 | May be involved in cell cycle regulation by chromatin remodeling. | Chromatin modification |

TABLE 8-continued

| | | | | |
|---|---|---|---|---|
| TOP2B | topoisomerase (DNA) II beta 180 kDa | essential for mammalian neural development; catalyses topological genomic changes essential for chromosome segregation, chromatin reorganization, | Chromatin modification | |
| TSN | translin | Translin and TRAX have been proposed to be involved in DNA recombination, chromosomal translocation and mRNA transport and translation. | Chromatin modification | |
| TSNAX | translin-associated factor X | Translin and TRAX have been proposed to be involved in DNA recombination, chromosomal translocation and mRNA transport and translation. | Chromatin modification | |
| TSPYL1 | TSPY-like 1 | chromatin remodeling factor | Chromatin modification | |
| UTX | \ubiquitously transcribed tetratricopeptide repeat, X chromosome\"" | Histone H3 methylation at Lys27 (H3K27 methylation) is a hallmark of silent chromatin, dUTX, specifically demethylates di- and trimethylated but not monomethylated H3K27, dUTX is intimately associated with actively transcribed genes | Chromatin modification | |
| WAPAL | wings apart-like homolog (Drosophila) | regulates heterochromatin organization; Wapl is a new regulator of sister chromatid resolution | Chromatin modification | |
| PHC3 | polyhomeotic homolog 3 (Drosophila) | Component of the Polycomb group (PcG) multiprotein PRC1 complex, a complex required to maintain the transcriptionally repressive state of many genes, including Hox genes, throughout development. PcG PRC1 complex acts via chromatin remodeling and modification of histones; | Chromatin modification | |
| CDYL | \chromodomain protein, Y-like\"" | Proteins encoded by this gene superfamily possess a chromodomain, a motif implicated in chromatin binding and gene suppression, and a catalytic domain believed to be involved in histone acetylation. | Chromatin modification | |
| CENPJ | centromere protein J | structural role for CPAP to maintain centrosome integrity and normal spindle morphology during cell division. | Chromatin modification | |
| TPK1 | thiamin pyrophosphokinase 1 | | Cofactor biosynthesis gene | |
| RFK | riboflavin kinase | | Cofactor biosynthesis gene | |
| VNN1 | vanin 1 | VNN1 gene product is involved in the thymus homing of bone marrow cells and in late adhesion steps of thymus homing under physiologic, noninflammatory conditions. Recently VNN1 gene upregulation has been linked to increased HDL level The product of CD1c gene is expressed on cortical thymocytes, immature myeloid dendritic cells, subset of normal peripheral B cells and activated T cells | Cofactor biosynthesis gene | |
| P4HA1 | \procollagen-proline, 2-oxoglutarate 4-dioxygenase (proline 4-hydroxylase), alpha polypeptide I\"" | When expressed intracellularly or exogenously delivered, P4HA1 significantly inhibited tumor growth in mice. Prolyl 4-hydroxylase (EC 1.14.11.2) plays a central role in collagen synthesis. It catalyzes the formation of 4-hydroxyproline in collagens by hydroxylation of proline residues in peptide linkages. The 4-hydroxyproline residues are essential for the folding of the newly synthesized procollagen polypeptide chain into triple helical molecules. | Collagen formation activity gene | Tumor suppressor activity gene |
| CHST2 | carbohydrate (N-acetylglucosamine-6-O) sulfotransferase 2 | CHST1 and CHST2 contribute to the generation of optimal L-selectin ligands in vascular endothelial cells at sites of inflammation and thus control inflammation. | Control of inflammation activity gene | |

TABLE 8-continued

| | | | | |
|---|---|---|---|---|
| PAPSS1 | 3'-phosphoadenosine 5'-phosphosulfate synthase 1 | 3'-phosphoadenosine 5'-phosphosulfate (PAPS) synthase (PAPSS) catalyzes the biosynthesis of PAPS which serves as the universal sulfonate donor compound for all sulfotransferase reactions. PAPSS forms PAPS in two sequential steps. First inorganic sulfate combines with ATP to form adenosine 5'-phosphosulfate (APS) and pyrophosphate catalyzed by ATP sulfurylase domain and in the second step, APS combines with another molecule of ATP to form PAPS and ADP catalyzed by APS kinase domain. The bifunctional PAPSS1 is comprised of NH2-terminal APS kinase domain (approximately 1-260 aa), and a COOH-terminal ATP sulfurylase domain (approximately 220-623 aa).. Many different endogenous and xenobiotic molecules are substrates for the sulfotransferases; sulfation affects many different physiological processes, including: 1) deactivation and bioactivation of xenobiotics, 2) inactivation of hormones and catecholamines, 3) structure and function of macromolecules, and 4) elimination of end products of catabolism. PAPS is the obligate cosubstrate that is synthesized in tissues to make available an "activated form" of sulfate for the sulfation reaction. | Detoxification Activity Gene | |
| PPA2 | pyrophosphatase (inorganic) 2 | Inorganic pyrophosphates are generated as byproducts of many biosynthetic reactions, including DNA and RNA synthesis, fatty acid and amino acid activation, and cyclic nucleotide synthesis. Inorganic pyrophosphatases (EC 3.6.1.1), such as PPA2, maintain the thermodynamic favorability of these reactions by catalyzing the hydrolysis of pyrophosphates into organic phosphates, which are then exported across the cell membrane (Curbo et al., 2006) | Detoxification Activity Gene | |
| RTN1 | reticulon 1 | In the presence of high RTN-1C levels, genotoxic drugs become ineffective as a consequence of the cytoplasm translocation of p53 protein, while the silencing of endogenous RTN-1C results in the potentiation of the genotoxic drugs action. Highly present in CNS. CNS stem cells? | Detoxification Activity Gene | |
| ATRN | attractin | in its natural serum form, it mediates the spreading of monocytes that becomes the focus for the clustering of nonproliferating T lymphocytes. Necessary for proper mitochondrial function and suppress oxidative stress. Atrn may play a protective role against environmental toxins | Detoxification Activity Gene, | mitochondrial function maintenance activity gene |
| PGK1 | phosphoglycerate kinase 1 | Glycolysis enzyme generating 1 molecule of ATP | Energy Generation | |
| GLS | glutaminase | human platelets. It is the major enzyme yielding glutamate from glutamine. Significance of the enzyme derives from its possible implication in behavior disturbances in which glutamate acts as a neurotransmitter. platelet glutaminase activity is entirely represented by the phosphate dependent glutaminase or glutaminase I, most probably localized in the mitochondrial platelet fraction and classified by kinetic analysis as a kidney-type form. The following step of the glutamine metabolizing pathway, allowing the entrance of the amino acid skeleton carbons in the Krebs cycle, | Energy generation | |

TABLE 8-continued

| | | | |
|---|---|---|---|
| | | might be catalyzed by both glutamate dehydrogenase and aspartate transaminase | |
| GLUD2 | glutamate dehydrogenase 2 | The following step of the glutamine metabolizing pathway, allowing the entrance of the amino acid skeleton carbons in the Krebs cycle, might be catalyzed by both glutamate dehydrogenase and aspartate transaminase | Energy generation |
| MUT | methylmalonyl Coenzyme A mutase | In mammalian cells only two enzymes are known to require cobalamin (vitamin B12) as a cofactor: methionine synthase, which uses methylcobalamin, and methylmalonyl-coenzyme A (CoA) mutase, which uses 5'-deoxyadenosyl-cobalamin (AdoCbl) Methylmalonyl-CoA mutase (MUT) (EC 5.4.99.2) is a mitochondrial enzyme that catalyzes the isomerization of methylmalonyl-CoA to succinyl-CoA. Methylmalonyl-CoA mutase occupies a key position in the pathway converting propionyl-CoA to succinyl-CoA, with the catabolism of isoleucine, methionine, threonine, and valine, as well as of cholesterol, odd chain fatty acids, thymine, and uracil leading to propionyl-CoA production. The enzyme is, therefore, part of a gluconeogenic pathway for converting amino acids, lipids, and pyrimidines to carbohydrates | Energy generation |
| PPAT | phosphoribosyl pyrophosphate amidotransferase | Phosphopantetheine adenylyltransferase (PPAT) is an essential enzyme in Coenzyme A biosynthesis. Biosynthesis of coenzyme A (CoA) from pantothenic acid (vitamin B5) is an essential universal pathway in prokaryotes and eukaryotes. COASY is a bifunctional enzyme that catalyzes the 2 last steps in CoA synthesis. | Energy generation |
| MTHFR | \5,10-methylenetetrahydrofolate reductase (NADPH)\"" | Methylenetetrahydrofolate reductase (EC 1.5.1.20) catalyzes the conversion of 5,10-methylenetetrahydrofolate to 5-methyltetrahydrofolate, a cosubstrate for homocysteine remethylation to methionine. | Homocysteine metabolism |
| MTR | 5-methyltetrahydrofolate-homocysteine methyltransferase | The remethylation of homocysteine to form methionine is catalyzed by the cytoplasmic enzyme 5-methyltetrahydrofolate-homocysteine S-methyltransferase (EC 2.1.1.13), which is also called methionine synthase. This enzyme requires methylcobalamin (MeCbl), a derivative of cobalamin, or vitamin B12, for activity. | Homocysteine metabolism |
| MTRR | 5-methyltetrahydrofolate-homocysteine methyltransferase reductase | Methionine is an essential amino acid required for protein synthesis and one carbon metabolism. Its synthesis is catalyzed by the enzyme methionine synthase. Methionine synthase eventually becomes inactive due to the oxidation of its cob(l)alamin cofactor. The protein encoded by this gene regenerates a functional methionine synthase via reductive methylation. It is a member of the ferredoxin-NADP(+) reductase (FNR) family of electron transferases. | Homocysteine metabolism |
| ADCY7 | adenylate cyclase 7 | Necessary for proper Eucaryotic signal transduction in platelets and other blood associated cells including natural killer cells, monocytes, and neutrophils | Immune health |
| NCKAP1L | NCK-associated protein 1-like | Expressed only in cells of hematopoietic origin. | Immune Health |

TABLE 8-continued

| | | | |
|---|---|---|---|
| ABCB7 | \ATP-binding cassette, sub-family B (MDR/TAP), member 7\"" | essential for hematopoiesis | Immune Health |
| AHI1 | Abelson helper integration site 1 | expression of mouse and human AHI1 was highest in the most primitive types of normal hematopoietic cells and was downregulated during early differentiation. This indicates that early precursors of blood cells are likely present in the peripheral blood. | Immune Health |
| CD164 | \CD164 molecule, sialomucin\"" | myeloid cells, T cells, epithelial cells, bone marrow stroma cells; adhesion molecule haem progenitor cells to stroma | Immune Health |
| CD200 | CD200 molecule | Normal brain and B-cell lines | Immune Health |
| CD74 | \CD74 molecule, major histocompatibility complex, class II invariant chain\"" | B cells, macrophages, monocytes, MHC class II positive cells | Immune health |
| CD83 | CD83 molecule | Activated B cells, activated T cells, circulating dendritic cells; | Immune health |
| CD8A | CD8a molecule | The CD8 antigen is a cell surface glycoprotein found on most cytotoxic T lymphocytes that mediates efficient cell-cell interactions within the immune system. The CD8 antigen, acting as a coreceptor, and the T-cell receptor on the T lymphocyte recognize antigen displayed by an antigen presenting cell (APC) in the context of class I MHC molecules. Cytotoxic T cells (TC cells, or CTLs) destroy virally infected cells and tumor cells, and are also implicated in transplant rejection. These cells are also known as CD8+ T cells, since they express the CD8 glycoprotein at their surface. Through interaction with helper T cells, these cells can be transformed into regulatory T cells, which prevent autoimmune diseases such as experimental autoimmune encephalomyelitis | Immune health |
| CERK | ceramide kinase | Catalyzes specifically the phosphorylation of ceramide to form ceramide 1-phosphate. Ceramide 1-Phosphate, a Mediator of Phagocytosis, might function as components of a 'rheostat' that regulates immune cell functions, including mast cell responsiveness, neutrophil and macrophage priming, chemotaxis, and survival of many types of immune cells. | Immune Health |
| CIAPIN1 | cytokine induced apoptosis inhibitor 1 | CIAPIN1, a necessary molecule for hematopoiesis that mediates antiapoptotic effects of various cytokines. | Immune Health |
| CIITA | \class II, major histocompatibility complex, transactivator\"" | Highly present in B-lymphocytes. This gene encodes a protein with an acidic transcriptional activation domain, 4 LRRs (leucine-rich repeats) and a GTP binding domain. The protein is located in the nucleus and acts as a positive regulator of class II major histocompatibility complex gene transcription, and is referred to as the "master control factor" for the expression of these genes. Mutations (lack of fuction) in this gene have been associated with bare lymphocyte syndrome type II (also known as hereditary MHC class II deficiency or HLA class II-deficient combined immunodeficiency), increased | Immune health |

TABLE 8-continued

| | | | |
|---|---|---|---|
| | | susceptibility to rheumatoid arthritis, multiple sclerosis, and possibly myocardial infarction. | |
| CLEC10A | \C-type lectin domain family 10, member A\"" | Probable role in regulating adaptive and innate immune responses. Binds in a calcium-dependent manner to terminal galactose and N-acetylgalactosamine units, linked to serine or threonine. | Immune Health |
| CPNE3 | copine III | copine III were expressed in the more immature neutrophil precursors | Immune Health |
| CPVL | \carboxypeptidase, vitellogenic-like\"" | CPVL protein expression was induced during maturation of monocytes into macrophages. | Immune Health |
| CTNNB1 | \catenin (cadherin-associated protein), beta 1, 88 kDa\"" | Hematopoietic stem cells (HSCs) have the ability to renew themselves and to give rise to all lineages of the blood. Reya et al. (2003) showed that the WNT signaling pathway has an important role in this process. Overexpression of activated beta-catenin expands the pool of HSCs in long-term cultures by both phenotype and function, beta-catenin is essential for fate decisions of skin stem cells: in the absence of beta-catenin, stem cells failed to differentiate into follicular keratinocytes and instead adopted an epidermal fate | Immune Health |
| CTSC | cathepasin C | Needed for activity and stability of neutrophil-derived serine proteases. | Immune Health |
| CYFIP2 | cytoplasmic FMR1 interacting protein 2 | Necessary for T-cell adhesion function | Immune Health |
| DPP8 | dipeptidyl-peptidase 8 | involve in immune functions | Immune Health |
| DPP9 | dipeptidyl-peptidase 9 | involve in immune functions | Immune Health |
| DPYSL2 | dihydropyrimidinase-like 2 | involved in T-cell polarization and migration. | Immune Health |
| DUSP5 | dual specificity phosphatase 5 | Mkp5-deficient cells produced greatly enhanced levels of proinflammatory cytokines during innate immune responses and exhibited greater T-cell activation than their wildtype counterparts. However, Mkp5-deficient T cells proliferated poorly upon activation, which resulted in increased resistance to experimental autoimmune encephalomyelitis. By contrast, Mkp5-deficient CD4+ (186940) and CD8+ (186910) effector T cells produced significantly increased levels of cytokines compared with wildtype cells, which led to much more robust and rapidly fatal immune responses to secondary infection with lymphocytic choriomeningitis virus. Zhang et al. (2004) concluded that MKP5 has a principal function in both innate and adaptive immune responses. | Immune Health |
| EDG1 | \endothelial differentiation, sphingolipid G-protein-coupled receptor, 1\"" | Adaptive immunity depends on T-cell exit from the thymus and T and B cells travelling between secondary lymphoid organs to survey for antigens. After activation in lymphoid organs, T cells must again return to circulation to reach sites of infection; however, the mechanisms regulating lymphoid organ exit are unknown. S1P1-dependent chemotactic responsiveness is strongly upregulated in T-cell development before exit from the thymus, whereas S1P1 is downregulated during peripheral lymphocyte activation, and this is associated with retention in lymphoid organs. | Immune Health |

TABLE 8-continued

| | | | |
|---|---|---|---|
| FCRL5 | Fc receptor-like 5 | May be involved in B-cell development and differentiation in peripheral lymphoid organs and may be useful markers of B-cell stages. May have an immunoregulatory role in marginal zone B-cells. | Immune Health |
| FER | fer (fps/fes related) tyrosine kinase (phosphoprotein NCP94) | Fps/Fes modulates the innate immune response of macrophages to LPS, in part, by regulating internalization and down-regulation of the TLR4 receptor complex. Fps/Fes and Fer are members of a distinct subfamily of cytoplasmic protein tyrosine kinases that have recently been implicated in the regulation of innate immunity, evidence for functional redundancy between Fps and Fer kinases in regulating hematopoiesis. | Immune Health |
| FLT3 | fms-related tyrosine kinase 3 | CD135 is a cytokine receptor expressed on the surface of hematopoietic progenitor cells. Signaling through CD135 plays a role in cell survival, proliferation, and differentiation. CD135 is important for lymphocyte (B cell and T cell) development, but not for the development of other blood cells (myeloid development). | Immune Health |
| NKTR | natural killer-tumor recognition sequence | The natural killer triggering receptor (NKTR) is involved in the recognition of tumor cells by large granular lymphocytes (LGLs) (Frey et al., 1991; Anderson et al., 1993). LGLs are a subpopulation of white blood cells that have the ability to kill target tumor cells by an MHC-independent mechanism. The protein product of the NKTR gene is present on the surface of LGLs and facilitates their binding to tumor targets. The gene codes for a protein of 150,000 Da, with a unique amino acid structure consisting of a 58-amino acid hydrophobic amino terminus followed by a cyclophilin-related domain. | Immune Health |
| PABPC4 | \poly(A) binding protein, cytoplasmic 4 (inducible form)\"" | might be necessary for regulation of stability of labile mRNA species in activated T cells. | Immune Health |
| PAG1 | phosphoprotein associated with glycosphingolipid microdomains 1 | Absence of external stimuli, the PAG-Csk complex transmits negative regulatory signals and thus may help to keep resting T cells in a quiescent state. PAG-CSK complex increases the signaling threshold required for initiating an immune response, thus helping to keep lymphocytes in a resting state. | Immune health |
| ADRBK2 | \adrenergic, beta, receptor kinase 2\"" | Specifically phosphorylates the agonist-occupied form of the beta-adrenergic and closely related receptors, in leukocytes from patients with active relapsing-remitting multiple sclerosis (MS) or with secondary progressive MS, GRK2 levels are significantly reduced, probable role in immune Maintenance and health | Immune health |
| GFI1 | growth factor independent 1 | Gfi1 maintained hematopoietic stem cell self-renewal, multilineage differentiation, and efficient reconstitution of hematopoiesis in transplanted hosts by restricting stem cell proliferation | Immune health |
| GPR34 | G protein-coupled receptor 34 | GPR34 is the functional mast cell lysoPS receptor. Lysophosphatidyl-L-serine (lysoPS) is thought to be an immunological regulator | Immune health |

TABLE 8-continued

| | | | |
|---|---|---|---|
| GPR44 | G protein-coupled receptor 44 | This receptor also called, CRTH2 is a receptor for PGD2, PGD2 functions as a neuromodulator as well as a trophic factor in the central nervous system. PGD2 is also involved in smooth muscle contraction/relaxation and is a potent inhibitor of platelet aggregation, receptor for prostaglandin (PG) D(2), which is a major mast cell product released during the allergic response. CRTH2 mediates the chemotaxis of eosinophils, basophils, and Th2 lymphocytes | Immune health |
| HHEX | hematopoietically expressed homeobox | Transcriptional repressor. May play a role in hematopoietic differentiation. | Immune health |
| ID2 | \inhibitor of DNA binding 2, dominant negative helix-loop-helix protein\"" | Id2 has an essential role in the generation of peripheral lymphoid organs and NK cells. D (inhibitor of DNA binding) HLH proteins lack a basic DNA-binding domain but are able to form heterodimers with other HLH proteins, thereby inhibiting DNA binding, importance of Id2 in regulating gene expression by CD8(+) T cells and the magnitude of effector responses, suggesting a mechanism involving Id protein- and E protein-mediated survival and differentiation of mature T cells, helix-loop-helix (HLH) transcription factor Id2 (inhibitor of DNA binding/differentiation 2) acts as a molecular switch in development of Langerhans cells (LCs), the cutaneous contingent of dendritic cells (DCs), and of specific DC subsets and B cells. | Immune health |
| IL10RA | \interleukin 10 receptor, alpha\"" | The protein encoded by this gene is a receptor for interleukin 10. This protein is structurally related to interferon receptors. It has been shown to mediate the immunosuppressive signal of interleukin 10, and thus inhibits the synthesis of proinflammatory cytokines. This receptor is reported to promote survival of progenitor myeloid cells through the insulin receptor substrate-2/PI 3-kinase/AKT pathway. Activation of this receptor leads to tyrosine phosphorylation of JAK1 and TYK2 kinases. | Immune health |
| IL7R | interleukin 7 receptor | This protein has been shown to play a critical role in the V(D)J recombination during lymphocyte development. This protein is also found to control the accessibility of the TCR gamma locus by STAT5 and histone acetylation. Knockout studies in mice suggested that blocking apoptosis is an essential function of this protein during differentiation and activation of T lymphocytes. The functional defects in this protein may be associated with the pathogenesis of the severe combined immunodeficiency (SCID). Receptor for interleukin-7. Also acts as a receptor for thymic stromal lymphopoietin | Immune health |
| IRF8 | interferon regulatory factor 8 | ICSBP in regulating the proliferation and differentiation of hematopoietic progenitor cells, antiviral responses associated with impaired production of IFN-gamma | Immune health |

TABLE 8-continued

| | | | |
|---|---|---|---|
| ITK | IL2-inducible T-cell kinase | Tec kinases Itk and Rlk provide important signals for terminal maturation, efficient cytokine production, and peripheral survival of NKT cells. This gene encodes an intracellular tyrosine kinase expressed in T-cells. The protein contains both SH2 and SH3 domains which are often found in intracellular kinases. It is thought to play a role in T-cell proliferation and differentiation. | Immune health |
| JAK1 | Janus kinase 1 (a protein tyrosine kinase) | Tyrosine kinase of the non-receptor type, involved in the IFN-alpha/beta/gamma signal pathway. Kinase partner for the interleukin (IL)-2 receptor. The Janus kinase-signal transducer and activator of transcription (Jak-Stat) pathway stands as a paradigm of how diverse extracellular signals can elicit rapid changes in gene expression in specific target cells. This pathway is widely used by members of the cytokine receptor superfamily, including those for the clinically important cytokines granulocyte colony-stimulating factor (G-CSF), erythropoietin, thrombopoietin, the interferons, and numerous interleukins, which makes it central to hematopoietic cell biology and hematologic therapy alike. Impaired lymphoid development in the absensce of JAK1 | Immune health |
| JMJD1A | jumonji domain containing 1A | Jmjd1a and Jmjd2c histone H3 Lys 9 demethylases regulate self-renewal in embryonic stem cells. | Immune health |
| JMJD2C | jumonji domain containing 2C | Jmjd1a and Jmjd2c histone H3 Lys 9 demethylases regulate self-renewal in embryonic stem cells. | Immune health |
| KIR2DS2 | \killer cell immunoglobulin-like receptor, two domains, short cytoplasmic tail, 2\"" | Killer-cell immunoglobulin-like receptors (KIRs), are a family of cell surface proteins found on important cells of the immune system called natural killer (NK) cells. They regulate the killing function of these cells by interacting with MHC class I molecules, which are expressed on all cell types. This interaction allows them to detect virally infected cells or tumor cells that have a characteristic low level of Class I MHC on their surface. Most KIRs are inhibitory, meaning that their recognition of MHC suppresses the cytotoxic activity of their NK cell. Only a limited number of KIRs have the ability to activate cells. This gene is an activating receptor. | Immune health |
| KLRC1 | \killer cell lectin-like receptor subfamily C, member 1\"" | Natural killer (NK) cells are lymphocytes that can mediate lysis of certain tumor cells and virus-infected cells without previous activation. They can also regulate specific humoral and cell-mediated immunity. NK cells preferentially express several calcium-dependent (C-type) lectins, which have been implicated in the regulation of NK cell function. | Immune health |
| L3MBTL3 | l(3)mbt-like 3 (*Drosophila*) | H-L(3)MBT protein, whose deletion is predicted to be responsible for myeloid hematopoietic malignancies, tumor suppressor gene. | Immune health |
| MEMO1 | mediator of cell motility 1 | Highly present in NK cells and other hematopoeitic cells | Immune health |
| NAGA | \N-acetylgalactos aminidase, alpha-\"" | Highly present in monocytes (Ascenta) what are the implications? lysosomal glycohydrolase that cleaves alpha-N-acetylgalactosaminyl moieties from glycoconjugates. | Immune health |
| NDFIP1 | Nedd4 family interacting protein 1 | Ndfip1 protein promotes the function of itch ubiquitin ligase to prevent T cell activation and T helper 2 cell-mediated inflammation. | Immune health |

TABLE 8-continued

| | | | | |
|---|---|---|---|---|
| NR1D2 | \nuclear receptor subfamily 1, group D, member 2\"" | Heme as the ligand | Immune health | |
| PRNP | \prion protein (p27-30) (Creutzfeldt-Jakob disease, Gerstmann-Strausler-Scheinker syndrome, fatal familial insomnia)\"" | PrPc is expressed on hematopoietic cells, including erythroid precursors. Prion protein is expressed on long-term repopulating hematopoietic stem cells and is important for their self-renewal. PrP is a marker for long-term hematopoietic stem cells. Prion protein expression may be involved in both the metabolism of copper and resistance to oxidative stress, neuroprotective role of cellular prion protein (PrPC) rion protein interferes with divalent metal Mn uptake and protects against Mn-induced oxidative stress | Immune health | Red blood cell health |
| PSCD1 | \pleckstrin homology, Sec7 and coiled-coil domains 1(cytohesin 1)\"" | Members of this family appear to mediate the regulation of protein sorting and membrane trafficking. The PSCD1 is highly expressed in natural killer and peripheral T cells, and regulates the adhesiveness of integrins at the plasma membrane of lymphocytes. | Immune health | |
| PTGER4 | prostaglandin E receptor 4 (subtype EP4) | This receptor can activate T-cell factor signaling. It has been shown to mediate PGE2 induced expression of early growth response 1 (EGR1), regulate the level and stability of cyclooxygenase-2 mRNA, and lead to the phosphorylation of glycogen synthase kinase-3. Knockout studies in mice suggest that this receptor may be involved in the neonatal adaptation of circulatory system, osteoporosis, as well as initiation of skin immune responses. Receptor for prostaglandin E2 (PGE2). The activity of this receptor is mediated by G(s) proteins that stimulate adenylate cyclase. Has a relaxing effect on smooth muscle. May play an important role in regulating renal hemodynamics, intestinal epithelial transport, adrenal aldosterone secretion, and uterine function. | Immune health | |
| PTPN11 | \protein tyrosine phosphatase, non-receptor type 11 (Noonan syndrome 1)\"" | Shp-2 is a widely expressed nonreceptor protein tyrosine phosphatase that participates early in hematopoietic development. | Immune health | |
| PTPN22 | \protein tyrosine phosphatase, non-receptor type 22 (lymphoid)\"" | This gene encodes a protein tyrosine phosphatase which is expressed primarily in lymphoid tissues. This enzyme associates with the molecular adapter protein CBL and may be involved in regulating CBL function in the T-cell receptor signaling pathway. | Immune health | |
| PTPRC | \protein tyrosine phosphatase, receptor type, C\"" | This gene is specifically expressed in hematopoietic cells. This PTP has been shown to be an essential regulator of T- and B-cell antigen receptor signaling. It functions through either direct interaction with components of the antigen receptor complexes, or by activating various Src family kinases required for the antigen receptor signaling. This PTP also suppresses JAK kinases, and thus functions as a regulator of cytokine receptor signaling. | Immune health | |

TABLE 8-continued

| | | | |
|---|---|---|---|
| RASSF5 | Ras association (RalGDS/AF-6) domain family 5 | Potential tumor suppressor. Seems to be involved in lymphocyte adhesion by linking RAP1A activation upon T cell receptor or chemokine stimulation to integrin activation. Isoform 2 stimulates lymphocyte polarization and the patch-like distribution of ITGAL/LFA-1, resulting in an enhanced adhesion to ICAM1. Together with RAP1A may participate in regulation of microtubule growth. The association of isoform 2 with activated RAP1A is required for directional movement of endothelial cells during wound healing | Immune health |
| RFX5 | \regulatory factor X, 5 (influences HLA class II expression)\"" | MHC class II molecules play a key role in the immune system. They present exogenous antigenic peptides to the receptor of CD4+ T-helper lymphocytes, thereby triggering the antigen-specific T-cell activation events required for the initiation and sustenance of immune responses.. Activates transcription from class II MHC promoters. Differentiation of hematopoietic stem and progenitors cells is an intricate process controlled in large part at the level of transcription. new transcriptional regulators of megakaryopoiesis. | Immune health |
| SENP6 | SUMO1/sentrin specific peptidase 6 | important in adult hematopoietic self-renewal | Immune health |
| SERPINB9 | \serpin peptidase inhibitor, clade B (ovalbumin), member 9\"" | The intracellular granzyme B inhibitor, proteinase inhibitor 9, is up-regulated during accessory cell maturation and effector cell degranulation, and its overexpression enhances CTL (cytotoxic lymphocyte) potency, the presence and subcellular localization of PI-9 in leukocytes and DCs are consistent with a protective role against ectopic or misdirected grB during an immune response. | Immune health |
| SOX4 | SRY (sex determining region Y)-box 4 | Sox4 contribute to the survival and proliferation of pro-B cells in response to extracellular signals. | Immune health |
| SPEN | \spen homolog, transcriptional regulator (Drosophila)\"" | The ability of Ott1 to affect hematopoietic cell fate and expansion in multiple lineages is a novel attribute for a spen family member and delineates Ott1 from other known effectors of hematopoietic development. | Immune health |
| SYBL1 | synaptobrevin-like 1 | VAMP-7 is a crucial component of granzyme B release and target cell killing in the NK cell | Immune health |
| TMPO | thymopoietin | It is possible that TCERG1 interacts with the nascent transcript (or RNP) and directly alters splicing decisions. This could be consistent with independent effects on transcription elongation and alternative processing. Alternatively, TCERG1 could work at | Immune health |
| VNN1 | vanin 1 | VNN1 gene product is involved in the thymus homing of bone marrow cells and in late adhesion steps of thymus homing under physiologic, noninflammatory conditions. Recently VNN1 gene upregulation has been linked to increased HDL level The product of CD1c gene is expressed on cortical thymocytes, immature myeloid dendritic cells, subset of normal peripheral B cells and activated T cells | Immune health |
| ZFX | \zinc finger protein, X-linked\"" | Zfx controls the self-renewal of embryonic and hematopoietic stem cells. Zfx as a shared transcriptional regulator of ESC and HSC, suggesting a common genetic basis of self-renewal in embryonic and adult SC. | Immune health |

TABLE 8-continued

| Gene | Name | Description | Category | |
|---|---|---|---|---|
| ZNF317 | zinc finger protein 317 | ZNF317 may play an important role in erythroid maturation and lymphoid proliferation | Immune health | Red blood cell health |
| ZNF589 | zinc finger protein 589 | Characterization of SZF1 implicates its role in hematopoiesis. | Immune health | |
| OGT | O-linked N-acetylglucosamine (GlcNAc) transferase (UDP-N-acetylglucosamine: polypeptide-N-acetylglucosaminyl transferase) | The regulation of topoisomerase I (topo I) activity is of prime importance for gene expression. It participates in DNA replication, transcription, recombination, and DNA repair, and serves as a target for anticancer drugs. Many proteins and enzymes are modified by O-linked beta-N-acetylglucosamine (O-GlcNAc), which exerts profound effects on their function. OGT is a central factor for T- and B-lymphocytes activation.. OGT participation in intracellular glycosylation is essential for embryonic stem cell viability | Immune Health | |
| PIK3R1 | \phosphoinositide-3-kinase, regulatory subunit 1 (p85 alpha)\"" | Important in adult hematopoietic self-renewal | Immune Health | |
| NKRF | NF-kappaB repressing factor | Interacts with a specific negative regulatory element (NRE) 5'-AATTCCTCTGA-3' to mediate transcriptional repression of certain NF-kappa-B responsive genes. NF-κB-repressing factor (NRF) is a constitutively expressed nuclear transcription factor that binds to beta interferon (IFN-β), interleukin-8 (IL-8), and inducible nitric oxide synthase (iNOS) promoters and represses the basal transcription of these genes | Inflammation control | |
| NR3C1 | \nuclear receptor subfamily 3, group C, member 1 (glucocorticoid receptor)\"" | The glucocorticoid receptor (GR) is a ligand-dependent transcription factor belonging to the nuclear hormone receptor superfamily. Due to its almost ubiquitous expression, GR plays an important role in many physiological and pathological processes. These include regulation of homeostasis, adaptation to stress, and modulation of central nervous system. In addition, GR is a major modulator of the immune system due to its proficient anti-inflammatory and immunosuppressive activity; and its function is important for proper regulation of many physiological processes. | Inflammation control | |
| ZCCHC11 | \zinc finger, CCHC domain containing 11\"" | ZCCHC11 is a unique TLR signal regulator, which interacts with TIFA after LPS treatment and suppresses the TRAF6-dependent activation of NF-kappaB. | Inflammation control | |
| SIRT1 | sirtuin (silent mating type information regulation 2 homolog) 1 (S. cerevisiae) | Longevity gene | Longevity gene | |
| YTHDF2 | \YTH domain family, member 2\"" | A polymorphism of the YTHDF2 gene (1p35) located in an Alu-rich genomic domain is associated with human longevity. | Longevity gene | |
| AP15 | apoptosis inhibitor 5 | Survival gene or anti-apoptotic gene | Longevity gene | |
| ARNT | aryl hydrocarbon receptor nuclear translocator | Bmal1-null mice lose circadian rhythmicity but also display tendon calcification and decreased activity, body weight, and longevity | Longevity gene | |

TABLE 8-continued

| | | | |
|---|---|---|---|
| FRAP1 | FK506 binding protein 12-rapamycin associated protein 1 | a gene expression signature associated with mammalian target of rapamycin (mTOR) activity that was down-regulated with age but preserved by CR in both WAT and heart, mammalian cells the mammalian TOR (mTOR) pathway plays a significant role in determining both resting oxygen consumption and oxidative capacity, mTOR activity may play an important role in determining the relative balance between mitochondrial and non-mitochondrial sources of ATP generation. | Longevity gene |
| HSPA9 | heat shock 70 kDa protein 9 (mortalin) | this member of the hsp70 family governs the longevity of worms and thus there are common pathways that determine mammalian and worm longevity | Longevity gene |
| POLG2 | \polymerase (DNA directed), gamma 2, accessory subunit\"" | Mitochondrial polymerase processivity subunit. Stimulates the polymerase and exonuclease activities, and increases the processivity of the enzyme. Binds to sc-DNA. | Mitochondrial DNA Health |
| OPA1 | optic atrophy 1 (autosomal dominant) | Mitochondrial health is defined by various parameters including fusion and fission events. In older cells, giant mitochondria accumulates. This is because of insufficient autophagy. These giants don't fuse with each other or with normal mitochondria and it was noticed that OPA1 is reduced in these giant mitochondria, mitochondria fuse and divide to change their morphology in response to a multitude of signals. During the past decade, work using yeast and mammalian cells has identified much of the machinery required for fusion and division, including the dynamin-related GTPases--mitofusins (Fzo1p in yeast) and OPA1 (Mgm1p in yeast) for fusion and Drp1 (Dnm1p) for division. Mitochondrial fusion requires coordinated fusion of the outer and inner membranes. This process leads to exchange of contents, controls the shape of mitochondria, and is important for mitochondrial function. OPA1 is a major organizer of the mitochondrial inner membrane and is required for the maintenance of cristae integrity. As the loss of OPA1 committed cells to apoptosis without any other stimulus. Olichon et al. (2003) proposed that OPA1 is involved in the sequestration of cytochrome c, and that OPA1 may be a target for mitochondrial apoptotic effectors. | Mitochondrial Health |
| PDSS2 | \prenyl (decaprenyl) diphosphate synthase, subunit 2\"" | PDSS2 gene, which encodes a subunit of decaprenyl diphosphate synthase, the first enzyme of the CoQ(10) biosynthetic pathway. | Mitochondrial Health |
| MFN1 | mitofusin 1 | The regulated equilibrium between mitochondrial fusion and fission is essential to maintain integrity of the organelle. Mechanisms of mitochondrial fusion are largely uncharacterized in mammalian cells. It is unclear whether OPA1, a dynamin-related protein of the inner membrane mutated in autosomal dominant optic atrophy, participates in fusion or fission. OPA1 promoted the formation of a branched network of elongated mitochondria, requiring the integrity of both its GTPase and C-terminal coiled-coil domain. Stable reduction of OPA1 levels by RNA interference resulted in small, fragmented, and scattered mitochondria. Levels of OPA1 did not affect | Mitochondrial Health |

TABLE 8-continued

| | | | |
|---|---|---|---|
| | | mitochondrial docking, but they correlated with the extent of fusion as measured by polyethylene glycol mitochondrial fusion assays. A genetic analysis proved that OPA1 was unable to tubulate and fuse mitochondria lacking the outer membrane mitofusin 1 but not mitofusin 2. Our data show that OPA1 functionally requires mitofusin 1 to regulate mitochondrial fusion and reveal a specific functional difference between mitofusin 1 and 2. | |
| MTRF1L | mitochondrial translational release factor 1-like | | Mitochondrial Health |
| NDUFC2 | \NADH dehydrogenase (ubiquinone) 1, subcomplex unknown, 2, 14.5 kDa\"" | Accessory subunit of the mitochondrial membrane respiratory chain NADH dehydrogenase (Complex I), that is believed to be not involved in catalysis. Complex I functions in the transfer of electrons from NADH to the respiratory chain. The immediate electron acceptor for the enzyme is believed to be ubiquinone. | Mitochondrial Health |
| NDUFS1 | \NADH dehydrogenase (ubiquinone) Fe—S protein 1.75 kDa (NADH-coenzyme Q reductase)\"" | Core subunit of the mitochondrial membrane respiratory chain NADH dehydrogenase (Complex I) that is believed to belong to the minimal assembly required for catalysis. Complex I functions in the transfer of electrons from NADH to the respiratory chain. The immediate electron acceptor for the enzyme is believed to be ubiquinone (By similarity). This is the largest subunit of complex I and it is a component of the iron-sulfur (IP) fragment of the enzyme. It may form part of the active site crevice where NADH is oxidized. | Mitochondrial Health |
| SDHD | \succinate dehydrogenase complex, subunit D, integral membrane protein\"" | Complex II of the respiratory chain, which is specifically involved in the oxidation of succinate, carries electrons from FADH to CoQ. The complex is composed of four nuclear-encoded subunits and is localized in the mitochondrial inner membrane. | Mitochondrial Health |
| ENC1 | ectodermal-neural cortex (with BTB-like domain) | Highly present in neuronal cells (and brain tissues from Ascenta-almost absent in other tissues) and involved in neuronal differentiation. Likely a Redox controlling protein | Nervous System Health |
| ADNP | activity-dependent neuroprotector | Involved in proper lipid metabolism, coagulation as well as in neurogenesis. Multiple Roles in Neuronal Differentiation and Maintenance, neuroprotective protein | Nervous System Health |
| AGTPBP1 | ATP/GTP binding protein 1 | zinc carboxypeptidase that contains nuclear localization signals and an ATP/GTP-binding motif that was initially cloned from regenerating spinal cord neurons of the mouse. Role in preventing neurodegeneration. | Nervous System Health |
| OAT | ornithine aminotransferase (gyrate atrophy) | OAT encodes the mitochondrial enzyme ornithine aminotransferase, which is a key enzyme is the pathway that converts arginine and ornithine into the major excitatory and inhibitory neurotransmitters glutamate and GABA. Vitamin B6 dependent enzyme. | Nervous system health |
| PTDSS1 | Phosphatidylserine synthase 1 | Phosphatidylserine (PS or PtdSer) is a phospholipid nutrient found in fish, green leafy vegetables, soybeans, and rice, and is essential for the normal functioning of neuronal cell membranes, activating protein kinase C (PKC), which has been shown to be involved in memory function. PS has been investigated in a small number of double-blind placebo trials and has been | Nervous system health |

TABLE 8-continued

| | | shown to increase memory performance in the elderly. Because of the potential cognitive benefits of phosphatidylserine, the substance is sold as a dietary supplement to people that believe they can benefit from an increased intake. | | |
|---|---|---|---|---|
| SPOCK2 | \sparc/osteonectin, cwcv and kazal-like domains proteoglycan (testican) 2\"" | May participate in diverse steps of neurogenesis | Nervous system health | |
| ADSS | adenylosuccinate synthase | carries out the first of a 2-step sequence in the biosynthesis of AMP from IMP. Plays an important role in the de novo pathway of purine nucleotide biosynthesis. AMP, is a nucleotide that is found in RNA. | Nucleotide Biosynthesis | |
| DCTD | dCMP deaminase | Supplies the nucleotide substrate for thymidylate synthetase which is the enzyme used to generate thymidine monophosphate (dTMP), which is subsequently phosphorylated to thymidine triphosphate for use in DNA synthesis and repair. | Nucleotide Biosynthesis | |
| HPRT1 | hypoxanthine phosphoribosyltransferase 1 (Lesch-Nyhan syndrome) | HPRT1 has a central role in the generation of purine nucleotides through the purine salvage pathway. HPRT1 catalyzes conversion of hypoxanthine to inosine monophosphate and guanine to guanosine monophosphate via transfer of the 5-phosphoribosyl group from 5-phosphoribosyl 1-pyrophosphate | Nucleotide biosynthesis | |
| PRPS1 | phosphoribosyl pyrophosphate synthetase 1 | Phosphoribosylpyrophosphate synthetase (PRPS; EC 2.7.6.1) catalyzes the phosphoribosylation of ribose 5-phosphate to 5-phosphoribosyl-1-pyrophosphate, which is necessary for the de novo and salvage pathways of purine and pyrimidine biosynthesis | Nucleotide biosynthesis | |
| CMPK | cytidylate kinase | Uridine monophosphate (UMP)/cytidine monophosphate (CMP) kinase (EC 2.7.4.4) catalyzes the phosphoryl transfer from ATP to UMP, CMP, and deoxy-CMP (dCMP), resulting in the formation of ADP and the corresponding nucleoside diphosphate. These nucleoside diphosphates are required for cellular nucleic acid synthesis. Enzyme deficiency in the salvage pathway of deoxyribonucleotide synthesis in mitochondria can cause mtDNA depletion syndromes. Maintenance of mitochondrial health. | Nucleotide Biosynthesis | Mitochondrial Health |
| ABCD3 | \ATP-binding cassette, sub-family D (ALD), member 3\"" | Peroxisome biogenesis | Peroxisome Health | |
| ABCD4 | \ATP-binding cassette, sub-family D (ALD), member 4\"" | Peroxisome biogenesis | Peroxisome Health | |
| PEX12 | peroxisomal biogenesis factor 12 | | Peroxisome Health | |
| PEX3 | peroxisomal biogenesis factor 3 | | Peroxisome Health | |
| RABGAP1L | RAB GTPase activating protein 1-like | Lower levles in platelet dysfunction | Platelet health | |

TABLE 8-continued

| | | | |
|---|---|---|---|
| CANX | calnexin | Calcium-binding protein that interacts with newly synthesized glycoproteins in the endoplasmic reticulum. It may act in assisting protein assembly and/or in the retention within the ER of unassembled protein subunits. It seems to play a major role in the quality control apparatus of the ER by the retention of incorrectly folded proteins. | Protein quality control |
| CLPX | ClpX caseinolytic peptidase X homolog (E. coli) | Clp ATPases are protein machines involved in protein degradation. The ClpXP ATPase-protease complex is a major component of the protein quality control machinery in the cell. | Protein quality control |
| DERL1 | \Der1-like domain family, member 1\"" | Derlin-1 is an important factor for the extraction of certain aberrantly folded proteins from the mammalian ER. Functional component of endoplasmic reticulum-associated degradation (ERAD) for misfolded lumenal proteins. May act by forming a chann | Protein quality control |
| DNAJA1 | \DnaJ (Hsp40) homolog, subfamily A, member 1\"" | Human DnaJ 2 (Hdj-2) is a co-chaperone of heat shock cognate 70 (Hsc70) which is localized to the cytosolic face of the ER. Necessary for proper folding of proteins and therefore proper functions of various proteins. | Protein quality control |
| EDEM3 | \ER degradation enhancer, mannosidase alpha-like 3\"" | enhances glycoprotein endoplasmic reticulum-associated degradation and mannose trimming, accelerates ERAD of misfolded glycoproteins. | Protein quality control |
| OMA1 | \OMA1 homolog, zinc metallopeptidase S. cerevisiae)\ "" | The integrity of the inner membrane of mitochondria is maintained by a membrane-embedded quality control system that ensures the removal of misfolded membrane proteins. Two ATP-dependent AAA proteases with catalytic sites at opposite membrane surfaces are key components of this proteolytic system, identify Oma1 as a novel component of the quality control system in the inner membrane of mitochondria. Mitochondrial protease | Protein quality control |
| CTSO | cathepsin O | normal cellular protein degradation and turnover | Protein quality control |
| HSP90AB1 | \heat shock protein 90 kDa alpha (cytosolic), class B member 1\"" | HSP90's function in the regulation and correct folding of at least 100 proteins[26] allows it to refold and/or degrade these products before they trigger cell death. They participate in the regulation of the stress response [2, 3] and, when associated with other co-chaperones, function in correctly folding newly synthesized proteins, stabilizing and refolding denatured proteins after stress, preventing misfolding and aggregation of unfolded or partially folded proteins, and assisting in protein transport across the endoplasmic reticulum (ER) and organellar membranes [4-8]. HSP90 members have key roles in the maturation of signal transduction proteins, like hormone receptors, various kinases, nitric oxide synthase and calcineurin | Protein quality control |
| HSPBAP1 | HSPB (heat shock 27 kDa) associated protein 1 | | Protein quality control |
| NGLY1 | N-glycanase 1 | N-glycanase is a highly conserved enzyme that catalyzes deglycosylation of misfolded N-linked glycoproteins by cleaving the glycan chain before the proteins are degraded by the proteasome | Protein quality control |

TABLE 8-continued

| | | | | |
|---|---|---|---|---|
| SACS | spastic ataxia of Charlevoix-Saguenay (sacsin) | The presence of heat-shock domains suggested a function for sacsin in chaperone-mediated protein folding. | Protein quality control | |
| SELS | selenoprotein S | SEPS1 gene helps in ridding the cell of misfolded proteins, preventing it from accumulating and subsequently resulting to inflammation. SEPS1 as a type of "garbage truck" that helps clear faulty proteins that accumulate in cells when they are placed under stress, causing inflammation to develop. | Protein quality control | |
| ST13 | suppression of tumorigenicity 13 (colon carcinoma) (Hsp70 interacting protein) | Hip facilitates may facilitate the chaperone function of Hsc/Hsp70 in protein folding and repair, and in controlling the activity of regulatory proteins such as steroid receptors and regulators of proliferation or apoptosis. | Protein quality control | |
| PDIA6 | \protein disulfide isomerase family A, member 6\"" | Formation and rearrangement of disulfide bonds during the correct folding of nascent proteins is modulated by a family of enzymes known as thiol isomerases, which include protein disulfide isomerase (PDI), | Protein quality control | |
| PDCL | phosducin-like | most members of the phosducin family act as co-chaperones with the cytosolic chaperonin complex (CCT) to assist in the folding of a variety of proteins from their nascent polypeptides | Protein quality control | |
| PDCL3 | phosducin-like 3 | most members of the phosducin family act as co-chaperones with the cytosolic chaperonin complex (CCT) to assist in the folding of a variety of proteins from their nascent polypeptides | Protein quality control | |
| AGA | aspartylglucos aminidase | key enzyme in the catabolism of N-linked oligosaccharides of glycoproteins. It cleaves the asparagine from the residual N-acetylglucosamines as one of the final steps in the lysosomal breakdown of glycoproteins. Needed for proper folding of proteins, particularly in the nervous system | Protein quality; Nervous system health | |
| ABCB10 | \ATP-binding cassette, sub-family B (MDR/TAP), member 10\"" | a mitochondrial inner membrane erythroid transporter involved in heme biosynthesis | Red blood cell health | |
| CAPRIN2 | caprin family member 2 | Involved in regulation of growth as erythroblasts shift from a highly proliferative state towards their terminal phase of differentiation. | Red blood cell health | |
| CYBRD1 | cytochrome b reductase 1 | Cybrd1 (duodenal cytochrome b) is not necessary for dietary iron absorption in mice. Likely participates in enhanced iron demand due to erythropoesis, ay be involved in extracellular ascorbate recycling in erythrocyte membranes. | Red blood cell health | |
| EDRF1 | Erythroid differentiation-related factor 1 | Transcription factor involved in erythroid differentiation. Involved in transcriptional activation of the globin gene. | Red blood cell health | |
| ERMAP | erythroblast membrane-associated protein (Scianna blood group) | Human Ermap is highly expressed in erythroid tissues and the protein localizes to the plasma membrane, particularly in sites of cell contact, and "cytoplasmic bodies." Ermap expression was restricted to fetal and adult erythroid tissues | Red blood cell health | |
| ETS1 | v-ets erythroblastos is virus E26 oncogene homolog 1 (avian) | ETS is responsible for erythroblast and fibroblast transformation. Critical for maturation of the T Cells. Tumor suppressor. | Red blood cell health | Immune Health |

TABLE 8-continued

Figure 6:
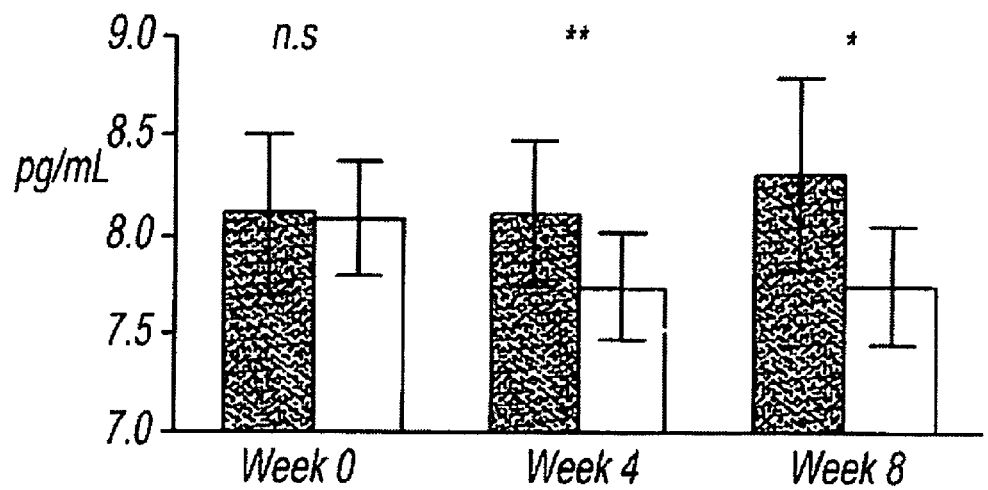
FIG. 6 is a graph depicting the effect the composition has on homocysteine levels.

| | | | |
|---|---|---|---|
| FLVCR1 | feline leukemia virus subgroup C cellular receptor 1 | Exports cytoplasmic heme. May be required to protect developing erythroid cells from heme toxicity. | Red blood cell health |
| ADD3 | adducin 3 (gamma) | ADD3 may have a role in erythroblasts and play an earlier role in erythropoiesis, hypertension. | Red blood cell health |
| IKZF1 | IKAROS family zinc finger 1 (Ikaros) | structure of a chromatin remodeling complex (PYR complex) with Ikaros as its DNA binding subunit that is specifically present in adult murine and human hematopoietic cells. Ikaros is involved in human adult or fetal erythroid differentiation as well as in the commitment between erythroid and myeloid cells. | Red blood cell health |
| MAEA | macrophage erythroblast attacher | The association of erythroblasts with macrophages plays a central role in the terminal maturation and enucleation of erythroblasts. MAEA mediates attachment of erythroblasts to macrophages. | Red blood cell health |
| MYB | v-myb myeloblastosis viral oncogene homolog (avian) | c-Myb is strictly required for expression of the c-Kit receptor in erythroid cells. The transcription factor c-Myb is expressed at high levels in immature progenitors of all hematopoietic lineages and is involved in the regulation of proliferation, differentiation, and survival, role for c-Myb as a factor promoting commitment to erythropoiesis and progression from early to late stages of differentiation (FIG. 6). We have shown that this function of c-Myb is probably not related to the cell cycle but rather to the control of a network of hematopoietic regulators. The expression of c-Kit in erythroid progenitors was tightly dependent on c-Myb levels. Finally, we demonstrated that c-Myb acts as a coordinator at the CFU-E stage by promoting further progression while supporting terminal cell divisions. | Red blood cell health |
| NFE2L3 | nuclear factor (erythroid-derived 2)-like 3 | Activates erythroid-specific, globin gene expression | Red blood cell health |
| SMAP1 | stromal membrane-associated protein 1 | SMAP-1 may have a stimulatory effect on stroma-supported erythropoiesis. | Red blood cell health |
| ZNF266 | zinc finger protein 266 | HZF1 play important roles in erythroid and megakaryocytic differentiation. Increased HZF1 mRNA expression was observed following erythroid differentiation of K562 cells induced by hemin or megakaryocytic differentiation of K562 cells induced by phorbol myristate acetate (PMA). Both of the antisense method and RNA interference assay revealed that | Red blood cell health |
| RNPS1 | \RNA binding protein S1, serine-rich domain\"" | Formation of transcription-induced R-loops poses a critical threat to genomic integrity throughout evolution., RNA binding protein RNPS1 alleviates ASF/SF2 depletion-induced genomic instability. RNPS1, that when overexpressed strongly suppresses the high molecular weight (HMW) DNA fragmentation, hypermutation, and G2 cell cycle arrest phenotypes of ASF/SF2-depleted cells. Involved in RENT2-dependent nonsense-mediated decay (NMD) of mRNAs containing premature stop codons. Also mediates increase of mRNA abundance and translational efficiency. Binds spliced mRNA 20-25 nt | RNA Quality Control |

TABLE 8-continued

| | | | |
|---|---|---|---|
| | | upstream of exon-exon junctions, low NMD efficiency is shown to be functionally related to the reduced abundance of the exon junction component RNPS1 | |
| PAPOLG | poly(A) polymerase gamma | This gene encodes a member of the poly(A) polymerase family which catalyzes template-independent extension of the 3' end of a DNA/RNA strand. This enzyme is exclusively localized in the nucleus and exhibits both nonspecific and CPSF (cleavage and polyadenylation specificity factor)/AAUAAA-dependent polyadenylation activity. | RNA Quality Control |
| DCP2 | DCP2 decapping enzyme homolog (*S. cerevisiae*) | Necessary for the degradation of mRNAs, both in normal mRNA turnover and in nonsense-mediated mRNA decay. | RNA Quality Control |
| DDX5 | DEAD (Asp-Glu-Ala-Asp) box polypeptide 5 | Nonsense mediated RNA degradation | RNA Quality Control |
| ERLIN2 | ER lipid raft associated 2 | key ERAD pathway component that may act as a substrate recognition factor. | RNA Quality Control |
| PARN | pol(A)-specific ribonuclease (deadenylation nuclease) | 3'-exoribonuclease that has a preference for poly(A) tails of mRNAs, thereby efficiently degrading poly(A) tails. Exonucleolytic degradation of the poly(A) tail is often the first step in the decay of eukaryotic mRNAs and is also used to silence certain maternal mRNAs translationally during oocyte maturation and early embryonic development. Interacts with both the 3'-end poly(A) tail and the 5'-end cap structure during degradation, the interaction with the cap structure being required for an efficient degradation of poly(A) tails. Involved in nonsense-mediated mRNA decay, a critical process of selective degradation of mRNAs that contain premature stop codons. | RNA quality control |
| UPF2 | UPF2 regulator of nonsense transcripts homolog (yeast) | Nonsense-mediated mRNA decay (NMD) represents a key mechanism to control the expression of wild-type and aberrant mRNAs. Phosphorylation of the protein UPF1 in the context of translation termination contributes to committing mRNAs to NMD. | RNA quality control |
| UPF3A | UPF3 regulator of nonsense transcripts homolog A (yeast) | They promote nonsense-mediated mRNA decay (NMD), and they also regulate translation efficiency. | RNA quality control |
| TRNT1 | \tRNA nucleotidyl transferase, CCA-adding, 1\"" | Adds and repairs the conserved 3'-CCA sequence necessary for the attachment of amino acids to the 3' terminus of tRNA molecules, using CTP and ATP as substrates. | RNA quality control |
| MAT2B | \methionine adenosyltransferase II, beta\"" | Methionine adenosyltransferase (MAT; S-adenosyl-L-methionine synthetase, EC 2.5.1.6)1 is an essential enzyme that catalyzes the synthesis of S-adenosylmethionine (AdoMet) from L-methionine (L-Met) and ATP (1, 2). AdoMet is the major methyl group donor, participating in the methylation of proteins, DNA, RNA, phospholipids, and other small molecules (reviewed in Refs. 3-5). In addition, AdoMet is the ultimate source of the propylamine moiety used in polyamine biosynthesis, and it serves as co-factor for other key enzymes in the one-carbon metabolism pathway. Methionine adenosyltransferase (MAT; EC 2.5.1.6) catalyzes the biosynthesis of S-adenosylmethionine (AdoMet) from methionine and ATP. MAT II is a broadly | SAM Biosynthetic machinary |

TABLE 8-continued

| | | | | |
|---|---|---|---|---|
| | | expressed MAT consisting of catalytic alpha and noncatalytic beta subunits encoded by MAT2A (601468) and MAT2B, respectively. Methionine adenosyltransferase (MAT) catalyzes the biosynthesis of S-adenosylmethionine (AdoMet), a key molecule in transmethylation reactions and polyamine biosynthesis. The MAT II isozyme consists of a catalytic alpha2 and a regulatory beta subunit. Down-regulation of the MAT II beta subunit expression causes a 6-10-fold increase in intracellular AdoMet levels. | | |
| SKIV2L2 | superkiller viralicidic activity 2-like 2 (*S. cerevisiae*) | mutation in skiv2l2 causes defects in cell proliferation, suggesting that skiv2l2 plays a role in regulating melanoblast proliferation during early stages of melanocyte regeneration. Skin | Skin Health | |
| ALDH18A1 | \aldehyde dehydrogenase 18 family, member A1\"" | Defects in this enzyme plays a role in neurodegeneration, joint laxity, skin hyperelasticity. Role in L-Proline biosynthesis | Skin health, | Nervous system health |
| KIT | Mast/stem cell growth factor receptor precursor | mobilization of hematopoetic stem cells into peripheral blood; marker for HSCs and MSCs | Stem cell health | |
| FLT3 | FMS-like tyrosine kinase 3) | restricted to CD34+ (high proportion of stem/progenitor cells) | Stem cell health | |
| ITK | IL2-inducible T-cell kinase | play a role in T cell proliferation and differentiation | Stem cell health | |
| CD74 | Cluster of Differentiation 74 | Hematopoietic Stem Cell survival pathway | Stem cell health | |
| HOXB2 | Homeobox B2, | Expressed in erythromegakaryocytic cells and Hematopoietic Stem Cells | Stem cell health | |
| CIAPIN1 | Cytokine induced apoptosis inhibitor 1 | Necessary for hematopoiesis | Stem cell health | |
| NOTCH4 | | hematopoietic stem/progenitor cells | Stem cell health | |
| NCOR1 | nuclear receptor co-repressor 1 | NCOR, a repressor or transcription, is a principal regulator in neural stem cells | Stem cell health | |
| PUM2 | pumilio homolog 2 (*Drosophila*) | Sequence-specific RNA-binding protein that regulates translation and mRNA stability by binding the 3'-UTR of mRNA targets. Its interactions and tissue specificity suggest that it may be required to support proliferation and self-renewal of stem cells by regulating the translation of key transcripts. | Stem cell health | |
| SLAIN2 | \SLAIN motif family, member 2\"" | Slain1 was expressed at the stem cell and epiblast stages of ESC differentiation | Stem cell health | |
| ACVR1 | \activin A receptor, type I\"" | Necessary for proper skeletal/bone formation; regulate the fate of hematopoietic progenitor and stem cells during development | Stem cell health | |
| PDCD4 | programmed cell death 4 (neoplastic transformation inhibitor) | The translation inhibitor programmed cell death 4 (Pdcd4) suppresses tumorigenesis and invasion. | Tumor suppresor | |
| AXIN2 | \axin 2 (conductin, axil)\"" | The Axin-related protein, Axin2, presumably plays an important role in the regulation of the stability of beta-catenin in the Wnt signaling pathway, like its rodent homologs, mouse conductin/rat axil. In mouse, conductin organizes a multiprotein complex of APC (adenomatous polyposis of the colon), beta-catenin, glycogen synthase kinase 3-beta, and conductin, which leads to the degradation of beta-catenin. Apparently, the deregulation of beta-catenin is an important event in the genesis of a number of malignancies. | Tumor suppressor function | |

TABLE 8-continued

| | | | |
|---|---|---|---|
| | | The AXIN2 gene has been mapped to 17q23-q24, a region that shows frequent loss of heterozygosity in breast cancer, neuroblastoma, and other tumors. Mutations in this gene have been associated with colorectal cancer with defective mismatch repair. | |
| AZIN1 | antizyme inhibitor 1 | It has been shown to regulate DNA methylation and has tumor suppressor activity, enhances the nonhomologous end-joining repair of DNA double-strand breaks in human oral cancer cells. | Tumor suppressor function |
| BECN1 | \beclin 1 (coiled-coil, myosin-like BCL2 interacting protein)\"" | UVRAG interacts with Beclin 1, leading to activation of autophagy and thereof inhibition of tumorigenesis. | Tumor suppressor function |
| CREBBP | CREB binding protein (Rubinstein-Taybi syndrome) | CBP has tumor suppressing activity. CBP may function as a 'master-switch' between energy storage and expenditure, long term memory. | Tumor suppressor function |
| CREBL2 | cAMP responsive element binding protein-like 2 | potential tumor suppressor | Tumor suppressor function |
| DIDO1 | death inducer-obliterator 1 | Putative transcription factor, weakly pro-apoptotic when overexpressed (By similarity). Tumor suppressor. | Tumor suppressor function |
| ING2 | \inhibitor of growth family, member 2\"" | Tumor suppressor | Tumor suppressor function |
| KRAS | v-Ki-ras2 Kirsten rat sarcoma viral oncogene homolog | Pfeifer (2001) noted an interesting parallel to the p53 (191170) tumor suppressor, which was initially described as an oncogene, carrying point mutations in tumors. Later it was discovered that it is, in fact, the wildtype copy of the gene that functions as a tumor suppressor gene and is capable of reducing cell proliferation | Tumor suppressor function |
| MTSS1 | metastasis suppressor 1 | putative metastasis suppressor gene | Tumor suppressor function |
| RB1 | retinoblastoma 1 (including osteosarcoma) | Key regulator of entry into cell division that acts as a tumor suppressor. Directly involved in heterochromatin formation by maintaining overall chromatin structure and, in particular, that of constitutive heterochromatin by stabilizing histone methylation. | Tumor suppressor function |
| SDCCAG1 | serologically defined colon cancer antigen 1 | can function as a tumor suppressor in human lung cancer cells. | Tumor suppressor function |
| SMAD4 | SMAD family member 4 | Common mediator of signal transduction by TGF-beta (transforming growth factor) superfamily; SMAD4 is the common SMAD (co-SMAD). Promotes binding of the SMAD2/SMAD4/FAST-1 complex to DNA and provides an activation function required for SMAD1 or SMAD2 to stimulate transcription. May act as a tumor suppressor. | Tumor suppressor function |
| STK3 | \serine/threonine kinase 3 (STE20 homolog, yeast)\"" | Novel tumor suppressor function. Stress-activated, pro-apoptotic kinase which, following caspase-cleavage, enters the nucleus and induces chromatin condensation followed by internucleosomal DNA fragmentation. | Tumor suppressor function |
| UVRAG | UV radiation resistance associated gene | UVRAG interacts with Beclin 1, leading to activation of autophagy and thereof inhibition of tumorigenesis. | Tumor suppressor function |
| WWOX | WW domain containing oxidoreductase | critical tumor suppressor gene | Tumor suppressor function |

TABLE 8-continued

| | | | | |
|---|---|---|---|---|
| FOXO1 | forkhead box O1 | Tumor suppressor and essential role in the Maintenance of hematopoetic stem cells | Tumor suppressor function | Immune Health |
| TFRC | \transferrin receptor (p90, CD71)\"" | | | |

The invention claimed is:

1. A method for modulating the expression of genes related to chromatin stability in a subject in need thereof, the method comprising:

administering to the subject an effective amount of a composition comprising a fruit ingredient, a vegetable ingredient and an herbal ingredient, wherein the fruit ingredient is pomegranate, present in a dosage range of about 5 mg/day to about 500 mg/day, and citrus bioflavonoids, present in a dosage range of about 25 mg/day to about 1000 mg/day, wherein the vegetable ingredient is asparagus, present in a dosage range of 25 mg/day to about 1000 mg/day, and watercress, present in a dosage range of about 5 mg/day to about 500 mg/day, and wherein the herbal ingredient is oregano, present in a dosage range of 25 mg/day to about 1000 mg/day, and rosemary, present in a dosage range of 25 mg/day to about 1000 mg/day; whereby the expression of genes related to chromatin stability is modulated.

2. The method of claim 1, wherein said administering step includes administering the composition to a subject in the form of three tablets, each tablet administered twice a day.

3. The method of claim 1, wherein said modulating step includes up-regulating the expression of chromatin stability-related genes.

4. A method of modulating the expression of DNA repair-related genes in a subject in need thereof, the method comprising:

administering to the subject an effective amount of a composition comprising a fruit ingredient, a vegetable ingredient and an herbal ingredient, wherein the fruit ingredient is pomegranate, present in a dosage range of about 5 mg/day to about 500 mg/day, and citrus bioflavonoids, present in a dosage range of about 25 mg/day to about 1000 mg/day, wherein the vegetable ingredient is asparagus, present in a dosage range of 25 mg/day to about 1000 mg/day, and watercress, present in a dosage range of about 5 mg/day to about 500 mg/day, and wherein the herbal ingredient is oregano, present in a dosage range of 25 mg/day to about 1000 mg/day, and rosemary present in a dosage range of 25 mg/day to about 1000 mg/day; whereby the expression of genes related to DNA repair is modulated.

5. The method of claim 4, wherein said administering step including administering the composition to a subject in the form of three tablets, each tablet administered twice a day.

6. The method of claim 4, wherein said modulating step includes up-regulating the expression of DNA repair-related genes.

7. A method for reducing the risk of chromatin damage, the method comprising:

administering an effective amount of a composition comprising a fruit ingredient, a vegetable ingredient and an herbal ingredient, wherein the fruit ingredient is pomegranate, present in a dosage range of about 5 mg/day to about 500 mg/day, and citrus bioflavonoids, present in a dosage range of about 25 mg/day to about 1000 mg/day, wherein the vegetable ingredient is asparagus, present in a dosage range of 25 mg/day to about 1000 mg/day, and watercress, present in a dosage range of about 5 mg/day to about 500 mg/day, and wherein the herbal ingredient is oregano, present in a dosage range of 25 mg/day to about 1000 mg/day, and rosemary present in a dosage range of 25 mg/day to about 1000 mg/day; and modulating the expression of genes to reduce the risk of chromatin damage with the administered effective amount of the composition.

8. The method of claim 7, wherein said administering step including administering the composition to a subject in the form of three tablets, each tablet administered twice a day.

9. The method of claim 7, wherein said modulating step includes up-regulating the expression of chromatin stability-related genes.

* * * * *

UNITED STATES PATENT AND TRADEMARK OFFICE
CERTIFICATE OF CORRECTION

| | | |
|---|---|---|
| PATENT NO. | : 7,939,115 B2 | Page 1 of 1 |
| APPLICATION NO. | : 12/059868 | |
| DATED | : May 10, 2011 | |
| INVENTOR(S) | : Huang et al. | |

It is certified that error appears in the above-identified patent and that said Letters Patent is hereby corrected as shown below:

Cover page, item (75) Inventors:

Delete "Edward W. Kahler" and replace with --Edward S. Kahler--

After Haeri Roh-Schmidt, delete "Long Beach" and replace with --Stockton--

After Shyam Ramakrishnan, delete "Long Beach" and replace with --La Habra--

Signed and Sealed this
Twenty-fifth Day of October, 2011

David J. Kappos
*Director of the United States Patent and Trademark Office*